United States Patent
Hibbard

(10) Patent No.: US 11,850,445 B2
(45) Date of Patent: Dec. 26, 2023

(54) SYSTEM AND METHOD FOR LEARNING MODELS OF RADIOTHERAPY TREATMENT PLANS TO PREDICT RADIOTHERAPY DOSE DISTRIBUTIONS

(71) Applicant: Elekta, Inc., Atlanta, GA (US)

(72) Inventor: Lyndon Stanley Hibbard, St. Louis, MO (US)

(73) Assignee: Elekta, Inc., Atlanta, GA (US)

(*) Notice: Subject to any disclaimer, the term of this patent is extended or adjusted under 35 U.S.C. 154(b) by 1112 days.

(21) Appl. No.: 16/330,662

(22) PCT Filed: Aug. 11, 2017

(86) PCT No.: PCT/US2017/046608
§ 371 (c)(1),
(2) Date: Mar. 5, 2019

(87) PCT Pub. No.: WO2018/048575
PCT Pub. Date: Mar. 15, 2018

(65) Prior Publication Data
US 2019/0192880 A1 Jun. 27, 2019

Related U.S. Application Data

(60) Provisional application No. 62/384,192, filed on Sep. 7, 2016.

(51) Int. Cl.
*A61N 5/10* (2006.01)
*G16H 30/20* (2018.01)
(Continued)

(52) U.S. Cl.
CPC ......... *A61N 5/1039* (2013.01); *A61N 5/1031* (2013.01); *G06N 3/045* (2023.01);
(Continued)

(58) Field of Classification Search
CPC .... A61N 5/1031; A61N 5/103; A61N 5/1038; A61N 5/1039
See application file for complete search history.

(56) References Cited

U.S. PATENT DOCUMENTS

| | | |
|---|---|---|
| 11,077,320 B1 | 8/2021 | Hibbard |
| 2012/0014507 A1 | 1/2012 | Wu et al. |

(Continued)

FOREIGN PATENT DOCUMENTS

| | | |
|---|---|---|
| CN | 104933245 | 9/2015 |
| CN | 105354611 | 2/2016 |

(Continued)

OTHER PUBLICATIONS

Wang, C. et al., "MRI-based Treatment Planning with Electron Density Information Mapped from CT Images: A Preliminary Study", Oct. 2008, Technology in Cancer Research and Treatment, vol. 7, No. 5, pp. 341-343 (Year: 2008).*

(Continued)

*Primary Examiner* — Christine H Matthews
(74) *Attorney, Agent, or Firm* — Schwegman Lundberg & Woessner, P.A.

(57) ABSTRACT

The present disclosure relates to systems and methods for developing radiotherapy treatment plans through the use of machine learning approaches and neural network components. A neural network is trained using one or more three-dimensional medical images, one or more three-dimensional anatomy maps, and one or more dose distributions to predict a fluence map or a dose map. During training the neural network receives a predicted dose distribution determined by the neural network that is compared to an expected dose distribution. Iteratively the comparison is performed until a predetermined threshold is achieved. The (Continued)

trained neural network is then utilized to provide a three-dimensional dose distribution.

22 Claims, 16 Drawing Sheets

(51) Int. Cl.
G16H 30/40 (2018.01)
G16H 40/63 (2018.01)
G16H 50/20 (2018.01)
G06N 3/084 (2023.01)
G06N 3/045 (2023.01)
G06N 3/08 (2023.01)

(52) U.S. Cl.
CPC .............. *G06N 3/08* (2013.01); *G06N 3/084* (2013.01); *G16H 30/20* (2018.01); *G16H 30/40* (2018.01); *G16H 40/63* (2018.01); *G16H 50/20* (2018.01)

(56) References Cited

U.S. PATENT DOCUMENTS

| | | | |
|---|---|---|---|
| 2013/0142310 | A1 | 6/2013 | Fahimian et al. |
| 2016/0129282 | A1 | 5/2016 | Yin et al. |
| 2016/0140300 | A1 | 5/2016 | Purdie et al. |
| 2017/0177812 | A1 | 6/2017 | Sjolund |
| 2019/0030370 | A1 | 1/2019 | Hibbard |
| 2019/0318474 | A1 | 10/2019 | Han |
| 2019/0333623 | A1 | 10/2019 | Hibbard |
| 2021/0244971 | A1 | 8/2021 | Hibbard |
| 2021/0308487 | A1 | 10/2021 | Hibbard |

FOREIGN PATENT DOCUMENTS

| | | |
|---|---|---|
| CN | 109843377 | 6/2019 |
| CN | 109843377 | 6/2022 |
| WO | WO-2014205128 A1 | 12/2014 |
| WO | WO-2015193776 A1 | 12/2015 |
| WO | 2016023786 | 2/2016 |
| WO | WO-2016081916 A1 | 5/2016 |
| WO | WO-2018048575 A1 | 3/2018 |
| WO | WO-2019023142 A1 | 1/2019 |
| WO | WO-2019212804 A1 | 11/2019 |
| WO | 2021159143 | 8/2021 |

OTHER PUBLICATIONS

Dias, Joana et al., "A genetic algorithm with neural network fitness function evaluation for IMRT beam angle optimization," 2013, Springer, CEJOR 22:431-455. (Year: 2013).*
"Australian Application Serial No. 2017324627, Response filed Jul. 17, 2019 to First Examination Report dated Jun. 11, 2019", 22 pgs.
"Australian Application Serial No. 2017324627, Subsequent Examiners Report dated Sep. 11, 2019", 11 pgs.
Georg, D, "Patient-specific IMRT verification using independent fluence-based dose calculation software: experimental benchmarking and initial clinical experience", Physics in Medicine and Biology, vol. 52, (2007), 4981-4992.
Gulliford, S, "Generating compensation designs for tangential breast irradiation with artificial neural networks", Physics n Medicine and Biology, vol. 47, (2002), 277-288.
Hernandez-Davila, V, "Determination of neuron fluence-to-dose conversion coefficients by means of artificial neural networks", Applied Radiation and Isotopes, vol. 83, (2014), 249-251.
Hua, K L, "Computer-aided classification of lung nodules on computed tomography images via deep learning technique", Onco Targets and Therapy. vol. 8, (2015), 2015-2022.
Kalantzis, G, "Toward IMRT 2D dose modeling using artificial neural networks: A feasibility study", Medical Physics, vol. 38, (10), (2011), 5807-5817.
Shin, H-C, "Interleaved text image deep mining on a very large-scale radiology database.", Proceedings of the IEEE Conference on Computer Vision and Pattern Recognition, (2015), 1090-1099.
U.S. Appl. No. 16/784,919, filed Feb. 7, 2020, Adversarial Prediction of Radiotherapy Treatment Plans.
"International Application Serial No. PCT US2017 046608, International Preliminary Report on Patentability dated Mar. 21, 2019", 8 pgs.
"Australian Application Serial No. 2017324627, First Examination Report dated Jun. 11, 2019", 4 pgs.
"Conditional Generative Adversarial Nets in TensorFlow", Agustinus Kristiadi's Blog, [Online]. Retrieved from the Internet: <URL: https://wiseodd.github.io/techblog/2016/12/24/conditional-gan-tensorflow/ >, 6 pgs.
"Imagenet", Stanford University Vision Lab, Accessed from Internet on Nov. 9, 2018 http://www.image-net.org/, (2016), 1 pg.
"International Application Serial No. PCT/US2018/043320, International Search Report dated Oct. 29, 2018", 6 pgs.
"International Application Serial No. PCT/US2018/043320, Written Opinion dated Oct. 29, 2018", 7 pgs.
"International Application Serial No. PCT/US2019/028720, International Search Report dated Oct. 16, 2019", 4 pgs.
"International Application Serial No. PCT/US2019/028720, Written Opinion dated Oct. 16, 2019", 8 pgs.
"Japanese Application Serial No. 2019-513074, Office Action dated Jan. 28, 2020", w/ English Translation, 4 pgs.
"Ray Tracing (graphics)", Wikipedia https://en.wikipedia.org/wiki/Ray_tracing_(graphics), (2019), 15 pgs.
"Russian Federation Application Serial No. 2019110153, Office Action dated Nov. 11, 2019", w/English Translation, 13 pgs.
"Russian Federation Application Serial No. 2019110153, Response filed Dec. 13, 2019 to Office Action dated Nov. 11, 2019", w/ English Claims, 70 pgs.
"VRad Deep Learning Algorithm Successfully Identifies Potential Intracranial Hemorrhaging (product announcement", https://www.vrad.com, Retrieved from internet: https://www.itnonline.com/content/vrad-deep-learning-algorithm-successfully-identifies-potential-intracranial-hemorrhaging, (Dec. 14, 2015), 2 pgs.
Abadi, Martin, et al., "Tensorflow: Large-scale machine learning on heterogeneous distributed systems", arXiv preprint arXiv:1603.04467, (2016), 19 pgs.
Androsova, E E, "Application of recursive recurrent neural networks", New information technologies in automated systems, (2016), 107-114.
Appenzoller, Lindsey M., et al., "Predicting dose-volume histograms for organs-at-risk in IMRT planning", Medical physics 39.12, (2012), 7446-7461.
Appenzoller, Lindsey M., et al., "Predicting dose-volume histograms for organs-at-risk in IMRT planning", Med. Phys. 39 (12), (Dec. 2012), pp. 7446-7461.
Babier, A, et al., "Knowledge-based automated planning with three-dimensional generative adversarial networks", Medical Physics, (Dec. 21, 2018), 15 pgs.
Bishop, Christopher M., "Pattern Recognition and Machine Learning", Springer-Verlag New York, (2006), 758 pgs.
Breedveld, Sebastiaan, et al., "The equivalence of multi-criteria methods for radiotherapy plan optimization", Physics in Medicine & Biology 54.23, (2009), 7199-7209.
Breedveld,, Sebastiaan, et al., "The equivalence of multi-criteria methods for radiotherapy plan optimization", Phys. Med. Biol. 54 (2009), (Nov. 17, 2009), pp. 7199-7209.
Bukovsky, Ivo, et al., "A Fast Neural Network Approach to Predict Lung Tumor Motion during Respiration for Radiation Therapy Applications", BioMed Research International vol. 2015, Article ID 489679, (2015), 3 pgs.
Chris, McIntosh, et al., "Fully automated treatment planning for head and neck radiotherapy using a voxel-based dose prediction and dose mimicking method", Physics in Medicine & Biology, vol. 62, No. 15, XP055416743, (Sep. 2, 2016), 5926-5944.
Creswell, Antonia, et al., "Generative Adversarial Networks: An Overview", IEEE Signal Processing Magazine 35.1, (2018), 53-65.
Dobler, Barbara, et al., "Direct machine parameter optimization for intensity modulated radiation therapy (IMRT) of oropharyngeal

(56) References Cited

OTHER PUBLICATIONS cancer—a planning study", Journal of Applied Clinical Medical Physics, vol. 10, No. 4,, (Fall 2009), pp. 4-15.

Glassner, A S, "An Introduction to Ray Tracing", Morgan-Kauffman Part 1 out of 2, (1989), 177 pgs.

Glassner, A S, "An Introduction to Ray Tracing", Morgan-Kauffman Part 2 out of 2, (1989), 176 pgs.

Goodfellow, Ian, et al., "Deep learning", vol. 1. Cambridge: MIT press, (2016), 802 pgs.

Goodfellow, Ian, et al., "Generative Adversarial Nets", Advances in Neural Information Processing Systems 27, Curran Associates, Inc., (Jun. 10, 2014), 9 pgs.

Goodfellow, Ian, "NIPS 2016 tutorial: Generative adversarial networks", arXiv preprint arXiv:1701.00160, (2016), 57 pgs.

Hardemark, Bjorn, et al., "Direct machine parameter optimization", Philips Medical Systems part Royal Philips Electronics whitepaper, (2004), 8 pgs.

Hastie, Trevor, et al., "The elements of statistical learning: data mining, inference, and prediction", Springer series in statistics, (2001), 764 pgs.

He, Kaiming, et al., "Identity mappings in deep residual networks", European Conference on Computer Vision. Springer, Cham, (2016), 15 pgs.

Hesse, Christopher, "Image-to-Image Translation in Tensorflow Make discriminators do your work for you", [Online]. Retrieved from the Internet: <URL: https://affinelayer.com/pix2pix/>, (Jan. 25, 2017), 12 pgs.

Ibragimov, B., et al., "Development of a Novel Deep Learning Algorithm for Autosegmentation of Clinical Tumor Volume and Organs at Risk in Head and Neck Radiation Therapy Planning", S226 International Journal of Radiation Oncology Biology Physics, (Oct. 1, 2016), p. 1147.

Ibragimov, B., et al., "Machine-Learning Based Segmentation of Organs at Risks for Head and Neck Radiotherapy Planning", [Online]. Retrieved from the Internet:<URL: http://onlinelibrary.wiley.com/doi/10.1118/1.4958186/full>, (Jun. 2016), 1 pg.

Isola, Phillip, et al., "Image-to-Image Translation with Conditional Adversarial Networks", arXiv:1611.07004 [cs.CV], (Nov. 22, 2017), 17 pgs.

Johnson, Hans J, et al., "The ITK Software Guide", (Jul. 25, 2019), 997 pgs.

Kak, A C, et al., "Principles of Computerized Tomographic Imagining Chapter 1", SIAM Philadelphia, (2001), 4 pgs.

Kak, A C, et al., "Principles of Computerized Tomographic Imagining Chapter 2", SIAM Philadelphia, (2001), 43 pgs.

Kak, A C, et al., "Principles of Computerized Tomographic Imagining Chapter 3", SIAM Philadephia, (2001), 64 pgs.

Kak, A C, et al., "Principles of Computerized Tomographic Imagining Chapter 4", SIAM Philadelphia, (2001), 63 pgs.

Kak, A C, et al., "Principles of Computerized Tomographic Imagining Chapter 5", SIAM Philadelphia, (2001), 25 pgs.

Kak, A C, et al., "Principles of Computerized Tomographic Imagining Chapter 6", SIAM Philadelphia, (2001), 71 pgs.

Kak, A C, et al., "Principles of Computerized Tomographic Imagining Chapter 7", SIAM Philadelphia, (2001), 22 pgs.

Kak, A C, et al., "Principles of Computerized Tomographic Imagining Chapter 8", SIAM Philapelphia, (2001), 26 pgs.

Kak, A C, et al., "Principles of Computerized Tomographic Imagining Index", SIAM Philadelphia, (2001), 6 pgs.

Kak, A C, et al., "Principles of Computerized Tomographic Imagining Introduction", Siam Philadelphia, (2001), 9 pgs.

Kang, John, et al., "Machine Learning Approaches for Predicting Radiation Therapy Outcomes: A Clinician's Perspective", International Journal of Radiation Oncology Biology Physics, (Jul. 27, 2015), pp. 1127-1135.

Krizhevsky, Alex, et al., "Imagenet classification with deep convolutional neural networks", Advances in neural information processings systems, (2012), 1-9.

Krizhevsky, Alex, et al., "Imagenet classification with deep convolutional neural networks", Advances in neural information processing systems, (2012), 9 pgs.

Kunze-Busch, M., et al., "Efficient SIB-IMRT planning of head and neck patients with Pinnacle—DMPO", Medicamundi 51/2+3 Nov. 2007, (Nov. 2007), pp. 95-99.

Lecun, Yann, et al., "Deep Learning", Nature vol. 521, (May 28, 2015), pp. 436-444.

Lecun, Yann, et al., "Deep learning", Nature, vol. 521. 7553, (2015), 436-444.

McIntosh, C, et al., "Contextual Atlas Regression Forests: Multiple-Atlas-Based Automated Dose Prediction in Radiation Therapy", IEEE Transactions on Medical Imaging, 15 pgs.

Mirza, Mehdi, et al., "Conditional generative adversarial nets", arXiv preprint arXiv:1411.1784, (2014), 7 pgs.

Murphy, K P, "Machine Learning: a Probabilistic Perspective", MIT Press, Cambridge, MA, USA Part 1 out of 2, (2012), 549 pgs.

Murphy, Kevin P, "Machine Learning A Probabilistic Perspective", MIT Press, Cambridge, MA, USA Part 2 out of 2, (2012), 549 pgs.

Nguyen, D, et al., "A feasibility study for predicting optimal radiation therapy dose distributions of prostate cancer patients from patient anatomy using deep learning", Scientific Reports www.nature.com/scientificreports, (Jan. 31, 2019), 10 pgs.

Nguyen, Dan, et al., "Dose Prediction with U-net: A Feasibility Study for Predicting Dose Distributions from Contours using Deep Learning on Prostate IMRT Patients", arXiv preprint arXiv:1709.09233, (2017), 17 pgs.

Nie, Dong, et al., "Estimating CT Image from MRI Data Using 3D Fully Convolutional Networks", (Sep. 27, 2016), 9 pgs.

Park, Seonyeong, et al., "Intra and Inter Fractional Variation Prediction of Lung Tumors Using Fuzzy Deep Learning", IEEE journal of Transitional Engineering in Health and Medicine, (Jan. 8, 2016), 12 pgs.

Rafid, Mahmood, et al., "Automated Treatment Planning in Radiation Therapy using Generative Adversarial Networks", Arxiv.Org, Cornell University Library, 201 Olin Library Cornell University Ithaca, NY 14853, XP081113459, (Jul. 17, 2018), 15 pgs.

Rit, S, et al., "The Reconstruction Toolkit (RTK), an open-source cone-beam CT reconstruction toolkit based o", 5 pgs.

Romeijn, Edwin H, et al., "A unifying framework for multi-criteria fluence map optimization models", Phys. Med. Biol. 49 (2004), (May 4, 2004), pp. 1991-2013.

Ronneberger, Olaf, et al., "U-Net Convolutional Networks for Biomedical Image Segmentation", Computer Science Department and BIOSS Centre for Biological Signalling Studies, University of Freiburg, Germany, (May 18, 2015), 8 pgs.

Ronneberger, Olaf, et al., "U-net: Convolutional networks for biomedical image segmentation", International Conference on Medical image computing and computer-assisted intervention. Springer, Cham, (2015), 1-8.

Shin, Hoo-Chang, et al., "Learning to Read Chest X-Rays: Recurrent Neural Cascade Model for Automated Image Annotation", National Institutes of Health, Bethesda, 20892-1182, (Mar. 28, 2016), 14 pgs.

Shirashi, S, et al., "Knowledge-based prediction of three-dimensional dose distributions for external beam radiotherapy", Medical Physics, 43(1), (2015), 378-287.

Shirley, P, et al., "Fundamentals of Computer Graphics", Chapter 10 Ray Tracing AK Peters, (2005), 785 pgs.

Tseng, Huan-Hsin, et al., "Deep reinforcement learning for automated radiation adaptation in lung cancer", Medical physics 44.12, (2017), 6690-6705.

Unkelbach, Jan, et al., "Optimization approaches to volumetric modulated arc therapy planning", Am. Assoc. Phys. Med. 42 (3), (Mar. 2015), 12 pgs.

Wachowicz, K, et al., "On the direct acquisition of beam's-eye-view mages in MRI for integration with external beam radiotherapy", Physics in Medicine, 11 pgs.

Wu, Binbin, et al., "Patient geometry-driven information retrieval for IMRT treatment plan quality control", Am Assoc Phys Med 36 12, (Nov. 6, 2009), 9 pgs.

(56) References Cited

OTHER PUBLICATIONS

Wu, Binbin, et al., "Patient geometry-driven information retrieval for IMRT treatment plan quality control", Medical physics 36.12, (2009), 5497-5505.
Yu, D, et al., "Automatic Speech Recognition: A Deep Learning Approach", Springer, (2015), 329 pages.
Zarepisheh, Masoud, et al., "A DVH-guided IMRT optimization algorithm for automatic treatment planning and adaptive radiotherapy replanning", Medical physics 41.6Part1, (2014), 061711-1-061711-14.
Zarepisheh, Masoud, et al., "A multicriteria framework with voxel dependent parameters for radiotherapy treatment plan optimization", Am. Assoc. Phys. Med.41 (4), (Apr. 2014), 11 pgs.
Zhu, Jun-Yan, et al., "Unpaired Image-to-Image Translation using Cycle-Consistent Adversarial Networks", IEEE International Conference on Computer Vision, (2017), 10 pgs.
Zhu, N, et al., "Deep Convolutional Neural Network Image Matching for Ultrasound Guidance in Radiotherapy", [Online], Retrieved from the Internet: <URL: http://onlinelibrary.wiley.com/doi/10.1118/1.4955603/abstract>, (Jun. 2016), 2 pgs.
Zhu, Xiaofeng, et al., "A planning quality evaluation tool for prostate adaptive IMRT based on machine learning", Am. Assoc. Phys. Med. 38 2, (Feb. 2011), pp. 719-726.
Zhu, Xiaofeng, et al., "A planning quality evaluation tool for prostate adaptive IMRT based on machine learning", Medical physics 38.2, (2011), 719-726.
Zuley, M L, et al., "Applying machine learning to radiotherapy planning for head & neck cancer", [Online] Retrieved from the Internet <URL:https://deepmind.com/blog/applying-machine-learning-radiotherapy-planning-head-neck-cancer/>, (Aug. 30, 2016), 3 pgs.
"Chinese Application Serial No. 201780062011.4, Office Action dated Oct. 19, 2021", w English translation, 20 pgs.
"Chinese Application Serial No. 201780062011.4, Office Action dated Jul. 30, 2020", w English translation, 23 pgs.
"European Application Serial No. 17755011.8, Communication pursuant to Article 94(3) EPC dated Jul. 1, 2020", 4 pgs.
"Chinese Application Serial No. 201780062011.4, Response filed Dec. 23, 2021 to Office Action dated Oct. 19, 2021", w English Claims, 18 pgs.
"Chinese Application Serial No. 201780062011.4, Response filed Mar. 9, 2022 to Examiner Phone Call", w English Claims, 16 pgs.
"U.S. Appl. No. 16/784,919, Notice of Allowance dated Apr. 15, 2021", 10 pgs.
"Chinese Application Serial No. 201780062011.4, Office Action dated Apr. 21, 2021", With English translation, 22 pages.
"U.S. Appl. No. 16/784,919, Corrected Notice of Allowability dated May 19, 2021", 4 pgs.
"European Application Serial No. 17755011.8, Communication Pursuant to Article 94(3) EPC dated May 6, 2021", 6 pgs.
"International Application Serial No. PCT US2021 070119, International Search Report dated May 19, 2021", 5 pgs.
"International Application Serial No. PCT US2021 070119, Written Opinion dated May 19, 2021", 6 pgs.
"U.S. Appl. No. 16/784,919, Corrected Notice of Allowability dated Jun. 30, 2021", 4 pgs.
"Chinese Application Serial No. 201780062011.4, Response filed Jul. 2, 2021 to Office Action dated Apr. 21, 2021", With English claims, 19 pgs.
Hibbard, Lyndon, "Adversarial Prediction of Radiotherapy Treatment Machine Parameters", Advances in Intelligent Data Analysis XIX; [Lecture Notes in Computer Science; Lect.Notes Computer], Springer InternationalPublishing, Cham,, (Oct. 1, 2020), 85-94.
"International Application Serial No. PCT/US2017/046608, International Search Report dated Jan. 15, 2018", 6 pgs.
"International Application Serial No. PCT/US2017/046608, Invitation to Pay Add'l Fees and Partial Search Report dated Nov. 8, 2017", 7 pgs.
"International Application Serial No. PCT/US2017/046608, Written Opinion dated Jan. 15, 2018", 6 pgs.
"Chinese Application Serial No. 201780062011.4, Response filed Dec. 11, 2020 to Office Action dated Jul. 30, 2020", w English claims, 20 pgs.
"European Application Serial No. 17755011.8, Response filed Jan. 7, 2021 to Communication pursuant to Article 94(3) EPC dated Jul. 1, 2020", 24 pgs.
"Beam's Eye View", Wikipedia https: en.wikipedia.org wiki Beam%27s_eye_view, (Accessed on Mar. 13, 2020), 1 pg.
"European Application Serial No. 17755011.8, Office Action dated Jan. 14, 2020", 3 pgs.
"European Application Serial No. 17755011.8, Response to Communication pursuant to Rules 161(1) and 162 EPC filed Mar. 20, 2020", 10 pgs.
"European Application Serial No. 17755011.8, Response filed Sep. 16, 2021 to Communication Pursuant to Article 94(3) EPC dated May 6, 2021", 16 pages.
"International Application Serial No. PCT US2021 070119, International Preliminary Report on Patentability dated Aug. 18, 2022", 8 pgs.
"U.S. Appl. No. 17/304,500, Non Final Office Action dated Feb. 13, 2023", 10 pgs.
"European Application Serial No. 21709317.8, Response to Communication pursuant to Rules 161 and 162 filed Mar. 8, 2023", 16 pgs.
"European Application Serial No. 17755011.8, Summons to Attend Oral Proceedings mailed Mar. 13, 2023", 7 pgs.
"U.S. Appl. No. 17/304,500, Response filed May 12, 2023 to Non Final Office Action dated Feb. 13, 2023", 11 pgs.
"U.S. Appl. No. 17/304,500, Non Final Office Action dated Jun. 15, 2023", 8 pgs.

\* cited by examiner

Axial View of Standard Treatment Plan Dose

SYSTEM AND METHOD FOR LEARNING MODELS OF RADIOTHERAPY TREATMENT PLANS TO PREDICT RADIOTHERAPY DOSE DISTRIBUTIONS

PRIORITY APPLICATIONS

This application is a U.S. National Stage Filing under 35 U.S.C. 371 from International Application No. PCT/US2017/046608, filed on Aug. 11, 2017, and published as WO2018/048575 on Mar. 15, 2018, which claims full benefit of and priority to United States Provisional Patent Application No. 62/384,192 filed Sep. 7, 2016 titled, "Learning Models of Radiotherapy Treatment Plans to Predict Therapy Dose Distributions," the benefit of priority of each of which is hereby claimed herein, and which applications and publication are hereby incorporated herein by reference in their entirety.

CROSS REFERENCE TO RELATED APPLICATIONS

This application claims full benefit of and priority to U.S. Provisional Patent Application No. 62/384,192 filed Sep. 7, 2016 titled, "Learning Models of Radiotherapy Treatment Plans to Predict Therapy Dose Distributions," the disclosure of which is fully incorporated herein by reference for all purposes.

FIELD AND BACKGROUND OF THE INVENTION

Field of the Invention

The present invention relates generally to radiation therapy systems. More particularly, embodiments of the disclosed invention address systems and methods for developing and implementing radiation treatment plans within a radiation treatment system that utilizes machine learning algorithms and neural networks.

Background of the Invention

Radiation therapy has been utilized to treat tumors in human (and animal) tissue. Intensity modulated radiotherapy (IMRT) and volumetric modulated arc therapy (VMAT) have become the standards of care in modern cancer radiation therapy, offering greater precision in target irradiation and greater protection for nearby sensitive tissues than earlier therapy methods. Unfortunately, creating individual patient treatment plans (e.g., either for IMRT, VMAT and the like) can be both a computationally intensive process and a trial-and-error process. Obtaining an optimal treatment plan that delivers a prescribed dose of radiation to the target while sparing critical organs or healthy surrounding tissues can require more time than is available in a busy clinic schedule and/or result in errors (e.g., over-dosed hot spots or undertreated tumor mass resulting from the proposed plan).

Furthermore, treatment plans are adjusted by manipulating program constraints and then recalculating a fluence map and alternatively, or in addition, a dose map. As used herein, a "fluence map" depicts localized deposition of energy in a patient. For example, a fluence map may depict the number of particles or photons per second of applied radiation crossing each voxel (volume element) in a 3D image, taking into account, for example, penetration through tissue. Also as used herein, a "dose map" depicts a radiation dose to be delivered to a patient from a radiotherapy device at a particular location (e.g., a beam angle), and utilizes specific radiation treatment device information such as gantry and multileaf collimator motion constraints or other delivery constraints of a radiotherapy system.

The effects of these manipulations on the recalculated fluence/dose map may be difficult to anticipate. For example, even the order in which program constraints are adjusted may affect the fluence/dose map. As a result, treatment planning often depends on the subjective judgments of experienced practitioners. Difficulties with ensuring treatment plan quality have been addressed by defining metrics (e.g., dose-volume histograms, overlap-volume histogram) and using these metrics may assist to identify related high-quality treatment plans. But even the most skilled practitioners cannot guarantee the optimality of a treatment plans or whether additional effort may identify a better treatment plan.

The trial-and-error processes of creating a treatment plan are well known in the art. For instance, initial treatment can be delayed because of the amount of time required by health care professionals in executing the treatment planning process. There have been studies that have shown that the treatment plans for VMAT, in comparison in IMRT, may require substantially more treatment planning time (e.g., up to a factor of 5 to 6.8 times as much planning time to obtain an optimized treatment plan as IMRT.

These approaches are particularly problematic for treatment clinics lacking deep local expertise and/or new equipment, and may be unsuitable for use in adaptive therapy. For example, a typical radiotherapy treatment plan may be developed prior to the beginning of a set of radiotherapy that will include multiple treatment sessions (e.g., up to 5 days a week) over many weeks (e.g., up to 8 weeks). In contrast, adaptive radiotherapy assesses changes in the patient relative to the original treatment plan; and to increase treatment precision, the original treatment plan is adapted. Adapting the original treatment plan requires repeated treatment planning. For instance, adaptive treatment planning requires additional imaging, treatment planning, in-room imaging, image registration and correction prior to treatment delivery. Clearly, radiation therapy treatment planning systems could benefit from more optimized and consistent treatment planning approaches.

Accordingly, there is a need for new systems and methods to efficiently generate fluence and dose maps in order to optimize treatment planning for a prescribed radiotherapy treatment. Such systems and methods could be aided by models of the treatment planning process derived from sets of exemplary treatment plans of the same kind.

SUMMARY

As used herein, a "machine learning algorithm" refers to any algorithm that can learn a model or a pattern based on existing information or knowledge, and predict or estimate output using input of new information or knowledge. Supervised learning is a branch of machine learning that infers a prediction model given a set of training data. Each individual sample of the training data is a pair containing a dataset (e.g., one or more images or imaging data) and a desired output value or dataset. A supervised learning algorithm analyzes the training data and produces a predictor function. The predictor function, once derived through training, is capable of reasonably predicting or estimating the correct output value or dataset for a valid input. The predictor function may be formulated based on various machine learning models, algorithms, and/or processes. The present disclosure relates to systems and methods for developing radiotherapy treatment plans though the use of machine learning approaches implemented through neural network components.

In one embodiment a radiation therapy treatment system is provided to predict a radiation therapy dose. The system includes an image acquisition device to acquire one or more three-dimensional medical images, a non-transitory machine-readable medium to store the one or more three-dimensional medical images, a neural network model, one or more three-dimensional anatomy maps and one or more three-dimensional dose distributions, and an image processing device. The image processing device is configured to train the neural network model to predict at least one of a fluence map and dose map based on the one or more three-dimensional medical images and the one or more three-dimensional anatomy maps, and to generate a three-dimensional dose distribution based on the neural network predictions.

In another embodiment a radiation therapy treatment system is provided to predict a radiation therapy dose that includes an image acquisition device to acquire a set of training data. The training data includes one or more three-dimensional medical images, a neural network model, one or more three-dimensional anatomy maps and one or more three-dimensional dose distributions. In addition, the system includes a non-transitory machine-readable medium to store the training data, a first neural network model, and a second neural network model. The system further includes an image processing device that is used to train the first neural network model using the training data to predict a first dose distribution. The image processor also trains a train the second neural network model using the training data to predict a second dose distribution. An error is determined by comparing the first dose distribution with the second dose distribution, and this error is used to further train the first neural network model.

A method to predict a radiation therapy dose is provided. The method includes receiving one or more three-dimensional medical images from an image acquisition device. The method further stores the three-dimensional images, a neural network model, one or more three-dimensional anatomy maps, and one or more three-dimensional dose distributions in a non-transitory computer-readable medium. Using a processor, the method trains the neural network to predict at least one of a fluence map and a dose map based on the one or more three-dimensional medical images and the one or more three-dimensional anatomy maps and one or more three-dimensional dose distributions. Then, the method generates a three-dimensional dose distribution based on the neural network predictions.

Beneficial effects of the embodiments of the present invention are numerous, and may include reducing expense and delay in planning and delivering radiation treatment to patients, reducing subjectivity in plan design, providing useful guidelines or insights for plan development, predicting performance of existing plans, and providing assistance for treatment clinics lacking deep local expertise. In any event, the process replaces the inefficient trial-and-error aspects of prior art implementations, and provides for improvements in planning accuracy and performance beyond previous implementations. Further, the accompanying drawings, which are incorporated in and constitute a part of this specification, illustrate several embodiments of the invention and together with the description, serve to explain the principles of the invention.

BRIEF DESCRIPTION OF THE DRAWINGS

The accompanying drawings, which constitute a part of this specification, illustrate several embodiments and, together with the description, serve to explain the disclosed principles.

DETAILED DESCRIPTION

Figure 1:
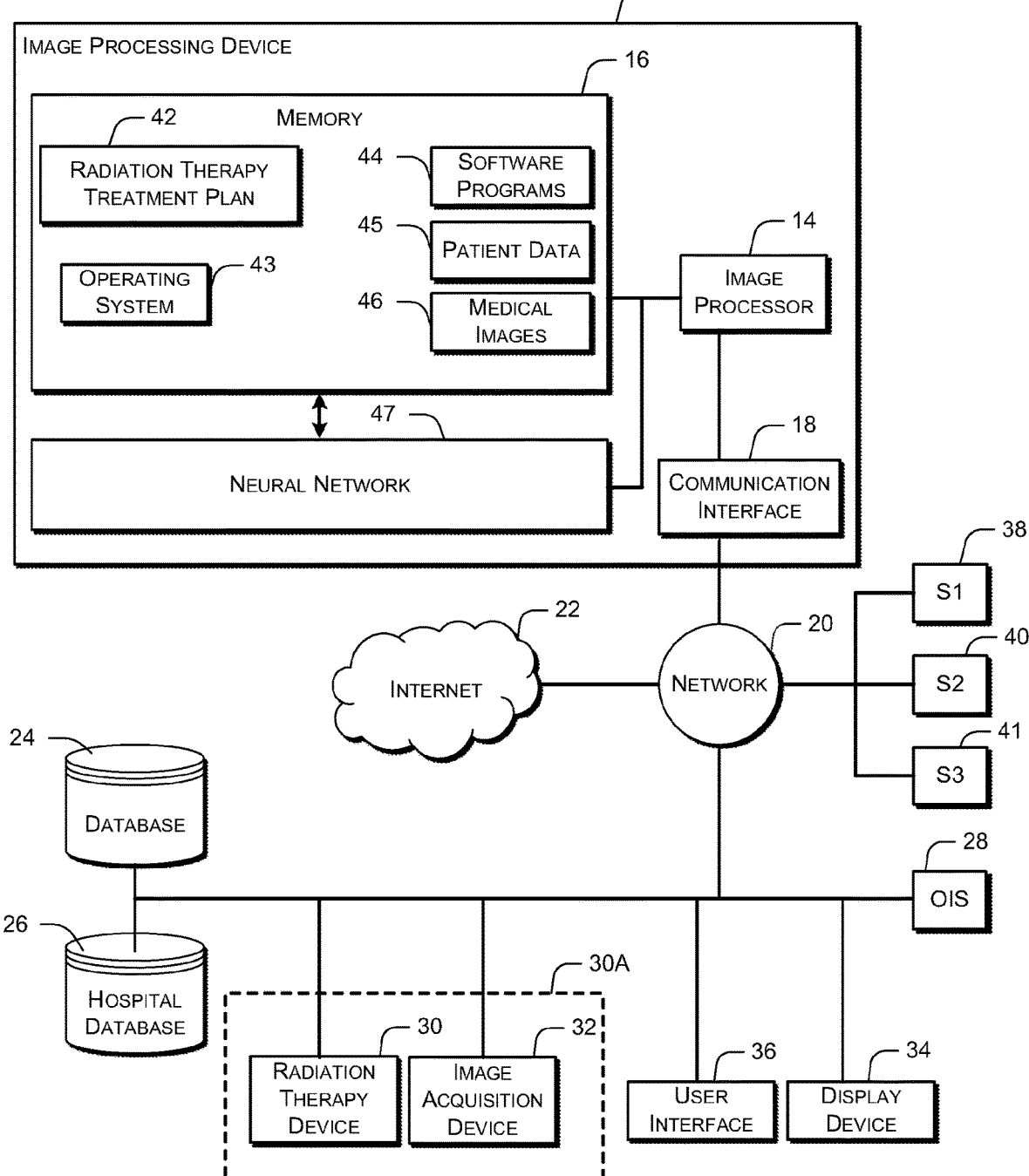
FIG. 1 illustrates an exemplary radiotherapy system, according to some embodiments of the present disclosure.

FIG. 1 illustrates an exemplary radiotherapy system 10 for providing radiation therapy to a patient. The radiotherapy system 10 includes an image processing device, 12. The image processing device 12 may be connected to a network 20. The network 20 may be connected to the Internet 22. The network 20 can connect the image processing device 12 with one or more of a database 24, a hospital database 26, an oncology information system (OIS) 28, a radiation therapy device 30, an image acquisition device 32, a display device 34, and a user interface 36. For example, the network 20 can connect the image processing device 12 with a database 24 or a hospital database 26, a display device 34, and a user interface 36. Also for example, the network 20 can connect the image processing device 12 with a radiation therapy device 30, an image acquisition device 32, a display device 34, and a user interface 36. The image processing device 12 is configured to generate radiation therapy treatment plans to be used by the radiation therapy device 30. Additionally, image processing device 12 may further comprise a user interface and display (not shown) communicatively coupled to the image processor 14.

As used herein, image data or imaging data refers to information that represents an image or view of a thing, including for example information that can be used to obtain or construct one or more images of the thing. For example, an image of a tumor may be represented by an array of pixel values, where each pixel is associated with image data for parameters such as luminance and color. Such parameters may use any of a variety of conventions or schemes; for example, color may be represented using the RGB, CMYK, CIE, or HSV color models. Image data may be stored in any format, including for example, one or more computer files in any of various image, ASCII, numerical, compressed, or standardized formats. An image may be multidimensional, including two-dimensional (2D) and three-dimensional (3D), and image data of many dimensions may be used to obtain images of fewer dimensions. For example, 3D image data may include data from which multiple different 2D images can be obtained or from which various 3D iso-surfaces can be rendered. Similarly, 4D image data (e.g. a time series of 3D images) may include data from which multiple different 3D or 2D images can be obtained.

The image processing device 12 may include a memory device 16, a processor 14 such as an image processor, a neural network 47, and a communication interface 18. The neural network 47 may comprise a deep convolutional neural network (DCNN) architecture, and may be implemented through software stored in the memory device 16, through external hardware (such as hardware accelerators or graphics processing units) coupled to the image processing device 12, or through a combination of stored software and external hardware. The memory device 16 may store computer-executable instructions in a non-transitory manner, such as an operating system 43, a radiation therapy treatment plans 42 (e.g., original treatment plans, adapted treatment plans and the like), software programs 44 (e.g., artificial intelligence, all or part of the neural network 47, and radiotherapy treatment plan software), and any other computer-executable instructions to be executed by the processor 14. In an embodiment the software programs 44 may convert medical images of one type (e.g., MRI) to another type (e.g., CT) by producing synthetic images, such as a pseudo-CT image. As used herein, a "medical image" refers to an image representing an object, such as an anatomical region of a person or animal that is useful for medical purposes, and includes a "patient image." Medical imaging data may be acquired by any type of imaging modalities, such as CT, magnetic resonance imaging (MRI), functional MRI (e.g., fMRI, DCE-MRI, and diffusion MRI), cone beam computed tomography (CBCT), Spiral CT, positron emission tomography (PET), single-photon emission computed tomography (SPECT), X-ray, optical tomography, fluorescence imaging, ultrasound imaging, and radiotherapy portal imaging, among others. Medical imaging data may be stored in any format, including DICOM format, jpeg, TIFF, GIF, EPS, PNG, PDF, scalable vector graphics, bitmaps, or any other conventional or nonconventional image data format. A "2D medical image" or "slice" may refer to a planar representation of an object, such as an anatomical region of a person or animal, from a certain viewpoint. A "3D medical image" may refer to an image representing a volume an object, such as an anatomical region of a person or animal. For instance, the software programs 44 may include image processing programs to train a predictive model for converting a medical image 46 in one modality (e.g., an MRI image) into a synthetic image of a different modality (e.g., a pseudo CT image); alternatively, the trained predictive model may convert a CT image into an MRI image. The memory device 16 may store data, including medical images (including medical imaging data) 46, patient data 45, and other data required to create and implement a radiation therapy treatment plan 42.

In addition to the memory 16 storing the software programs 44, it is contemplated that software programs 44 may be stored on a removable computer medium, which may be used in addition to or in replacement for a fixed storage medium, the removable medium including devices such as a hard drive, a computer disk, a CD-ROM, a DVD, a HD, a Blu-Ray DVD, USB flash drive, a SD card, a memory stick, or any other suitable non-transitory medium coupled to the processor 14. The software programs 44 when downloaded to or accessible to image processing device 12 may be executed by image processor 14.

The processor 14 may be communicatively coupled to the memory device 16 and neural network 47, and the processor 14 may be configured to execute computer executable instructions stored thereon. The processor 14 may send or receive medical images to any area of memory 16 or neural network 47 such as the medical images stored in location 46. For example, the processor 14 may receive medical images from the image acquisition device 32 through network 20 via the communication interface 18 to be stored in memory 16. The processor 14 may also send medical images stored in memory 16, 46 via the communication interface 18 to the network 20 be either stored in database 24 or the hospital database 26.

Further, the processor 14 may utilize software programs 44 (e.g., a treatment planning software) and the neural network 47 along with the medical images 46 and patient data 45 to create a radiation therapy treatment plan 42. Medical images 46 may include imaging data such as data for interpretation or processing of the image, data associated with a patient anatomical region, organ, or volume of interest, and segmentation data. Patient data 45 may include information such as (1) functional organ modeling data (e.g., serial versus parallel organs, appropriate dose response models, and the like); (2) radiation dosage data (e.g., dose-volume histogram (DVH) information; or (3) other clinical information about the patient and course of treatment (e.g., other surgeries, chemotherapy, and previous radiotherapy).

In addition, the processor 14 may utilize software programs to generate intermediate data such as updated parameters to be used, for example, by a model implemented by the neural network 47; or generate intermediate 2D or 3D images, which may then subsequently be stored in memory 16. The processor 14 may subsequently then transmit the executable radiation therapy treatment plan 42 via the communication interface 18 via the network 20 to the radiation therapy device 30, where the radiation therapy plan will be used to treat a patient with radiation. In addition, the processor 14 may execute software programs 44 to implement functions such as image conversion, image segmentation, deep learning, neural network training, neural network evaluation, and artificial intelligence. For instance, the processor 14 may execute software programs 44 that train or contour a medical image; such software 44 that when executed may train a boundary detector, or utilize a shape dictionary.

The processor 14 may comprise a processing device, and may include one or more general-purpose processing devices such as a microprocessor, a central processing unit (CPU), a graphics processing unit (GPU), an accelerated processing unit (APU), a hardware accelerator, or the like. More particularly, the processor 14 may include a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 14 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 14 may be a special-purpose processor, rather than a general-purpose processor. The processor 14 may include one or more known processing devices, such as a microprocessor from the Pentium™ Core™, Xeon™, or Itanium® family manufactured by Intel™, the Turion™, Athlon™ Sempron™, Opteron™, FX™, Phenom™ family manufactured by AMD™, or any of various processors manufactured by Sun Microsystems. The processor 14 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 14 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processor 14 can execute sequences of computer program instructions, stored in memory 16, to perform various operations, processes, methods that will be explained in greater detail below.

The memory device 16 can store medical images (including imaging data) 46. In some embodiments, the medical images 46 may include one or more MRI images (e.g., 2D MRI, 3D MRI, 2D streaming MRI, 4D MRI, 4D volumetric MRI, 4D cine MRI, and the like), functional MRI images (e.g., fMRI, DCE-MRI, diffusion MRI), digital camera images (e.g., in JPEG, RAW, TIFF, or GIF format), computer graphics images, Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images), user-generated images, and the like. Further, the medical images 46 may also include training images, expected results images, ground truth images, fictitious images, processed images, and contoured images. In an embodiment, the medical images 46 may be received from a database 24, 26. In another embodiment, the medical images 46 may be received from the image acquisition device 32. Accordingly, image acquisition device 32 may include any device that can provide imaging data, including for example, an MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining medical images of the patient. The medical images (including medical imaging data) 46 may be received and stored in any type of data or any type of format that the image processing device 12 may use to perform operations consistent with the disclosed embodiments. The memory device 16 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processor 14, or any other type of computer device. The computer program instructions can be accessed by the processor 14, read from the ROM, or any other suitable memory location, and loaded into the RAM for execution by the processor 14. For example, the memory 16 may store one or more software applications. Software applications stored in the memory 16 may include, for example, an operating system 43 for common computer systems as well as for software-controlled devices. Further, the memory 16 may store an entire software application, or only a part of a software application, that are executable by the processor 14. For example, the memory device 16 may store one or more radiation therapy treatment plans 42. In yet another embodiment, the medical image data 46 may be received from both a database and a device (e.g. a device provides an updated version of an image stored in the database by identifying changed features).

The image processing device 12 can communicate with the network 20 via the communication interface 18, which is communicatively coupled to the processor 14, the memory 16, and neural network 47. The communication interface 18 may provide communication connections between the image processing device 12 and radiotherapy system 10 components (e.g., permitting the exchange of data with external devices). For instance, the communication interface 18 may in some embodiments have appropriate interfacing circuitry to connect to the user interface 36, which may be a hardware keyboard, a keypad, or a touch screen through which a user may input information into radiotherapy system 10.

Communication interface 18 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 18 may include one or more digital and/or analog communication devices that permit image processing device 12 to communicate with other machines and devices, such as remotely located components, via the network 20.

The network 20 may provide the functionality of a local area network (LAN), a wireless network, a cloud computing environment (e.g., software as a service, platform as a service, infrastructure as a service, etc.), a client-server, a wide area network (WAN), and the like. For example, network 20 may be a LAN or a WAN that may include other systems S1 (38), S2 (40), and S3 (41). Systems S1, S2, and S3 may be identical to image processing device 12 or may be different systems. In some embodiments, one or more of systems in network 20 may form a distributed computing/simulation environment that collaboratively performs the embodiments described herein. In some embodiments, one or more systems S1, S2, and S3 may include a CT scanner that obtain CT images (e.g., medical images 46). In addition, network 20 may be connected to internet 22 to communicate with servers and clients that reside remotely on the internet. In additional embodiments, one or more systems S1, S2, and S3 may include externally-accessible neural networks or related computation facilities.

Therefore, network 20 can allow data transmission between the image processing device 12 and a number of various other systems and devices, such as the OIS 28, the radiation therapy device 30, and the image acquisition device 32. Further, data generated by the OIS 28 and/or the image acquisition device 32 may be stored in the memory 16, the database 24, and/or the hospital database 26. The data may be transmitted/received via network 20, through communication interface 18 in order to be accessed by the processor 14, as required.

The image processing device 12 may communicate with database 24 through network 20 to send/receive a plurality of various types of data stored on database 24. For example, database 24 may include machine data that is information associated with a radiation therapy device 30, image acquisition device 32, or other machines relevant to radiotherapy. Machine data information may include radiation beam size, arc placement, beam on and off time duration, control points, segments, multi-leaf collimator (MLC) configuration, gantry speed, MRI pulse sequence, and the like. Database 24 may be a non-transitory storage device. One skilled in the art would appreciate that database 24 may include a plurality of devices located either in a central or a distributed manner.

In some embodiments, database 24 may include a processor-readable non-transitory storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

Image processor 14 may communicate with database 24 to read images into memory 16 or store images from memory 16 to database 24. For example, the database 24 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, etc.) that the database 24 received from image acquisition device 32. Database 24 may store data to be used by the image processor 14 when executing software program 44, or when creating radiation therapy treatment plans 42. The image processing device 12 may receive the imaging data 46 (e.g., 2D MRI slice images, CT images, 2D Fluoroscopy images, X-ray images, 3DMRI images, 4D MRI images, etc.) either from the database 24, the radiation therapy device 30 (e.g., a MRI-Linac), and or the image acquisition device 32 to generate a treatment plan 42.

In an embodiment, the radiotherapy system 10 can include an image acquisition device 32 that can acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 32 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the imaging acquisition device 32 can be stored within database 24 as either imaging data and/or test data. By way of example, the images acquired by the imaging acquisition device 32 can be also stored by the image processing device 12, as medical image data 46 in memory 16.

In an embodiment, for example, the image acquisition device 32 may optionally be integrated with the radiation therapy device 30 as a single apparatus 30A (e.g., a MRI device combined with a linear accelerator, also referred to as an "MM-Linac." Such an MRI-Linac can be used, for example, to determine a location of a target organ or a target tumor in the patient, so as to direct radiation therapy accurately according to the radiation therapy treatment plan 42 to a predetermined target.

The image acquisition device 32 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location). In an example, the image acquisition device 32 can acquire a 2D slice in any orientation. For example, an orientation of the 2D slice can include a sagittal orientation, a coronal orientation, or an axial orientation. The processor 14 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 32 in "real-time" while a patient is undergoing radiation therapy treatment, for example, when using the radiation therapy device 30. "Real-time" meaning acquiring the data in at least milliseconds or less.

The image processing device 12 may generate and store radiation therapy treatment plans 42 for one or more patients. The radiation therapy treatment plans 42 may provide information about a particular radiation dose to be applied to each patient. The radiation therapy treatment plans 42 may also include other radiotherapy information, such as beam angles, dose-histogram-volume information, delivery parameters such as the number of radiation beams to be used during therapy, the maximum dose per beam or gantry speed, and the like.

The image processor 14 may generate the radiation therapy treatment plan 42 by using software programs 44 such as treatment planning software, such as MONACO®, manufactured by Elekta, Inc., of Atlanta, Georgia. In order to generate the radiation therapy treatment plans 42, the image processor 14 may communicate with the image acquisition device 32 (e.g., a CT device, a MRI device, a PET device, an X-ray device, an ultrasound device), memory 16, or database 24 to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR (that is, delineation of the structures of organs at risk from the nearby treatment volumes) may be performed when the OAR is close to the target tumor. In addition, if the target tumor is close to the OAR (e.g., prostate in near proximity to the bladder and rectum), then by segmenting the OAR from the tumor, the treatment planning device may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 32 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution.

Examples of treatment plan parameters include volume delineation parameters (e.g., which define target volumes or contour-sensitive structures), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45Gy, ≤55Gy and <54Gy, respectively). The result of inverse planning may constitute a radiation therapy treatment plan 42 that may be stored in memory 16 or database 24. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 12 can generate a tailored radiation therapy treatment plan 42 having these parameters in order for the radiation therapy device 30 to provide radiotherapy treatment to the patient.

In addition, the radiotherapy system 10 may include a display device 34 and a user interface 36. The display device 34 may include one or more display screens that display medical images, interface information, treatment planning parameters (e.g., contours, dosages, beam angles, and the like), treatment plans, a target, localizing a target and/or tracking a target, or any information related to the user or patient. The user interface 36 may be a keyboard, a keypad, a mouse, a touch pad, a touch screen or any type of device that a user may input information to radiotherapy system 10. Alternatively, the display device 34 and the user interface 36 may be integrated into a device such as a tablet computer, e.g., Apple iPad®, Lenovo Thinkpad®, Samsung Galaxy®, and the like.

Furthermore, any and all components of the radiotherapy system 10 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 12, the OIS 28, or the image acquisition device 32 could be implemented as a virtual machine. Given the processing power, memory, and computational capability available, the entire radiotherapy system 10 could be implemented as a virtual machine.

Figure 2:
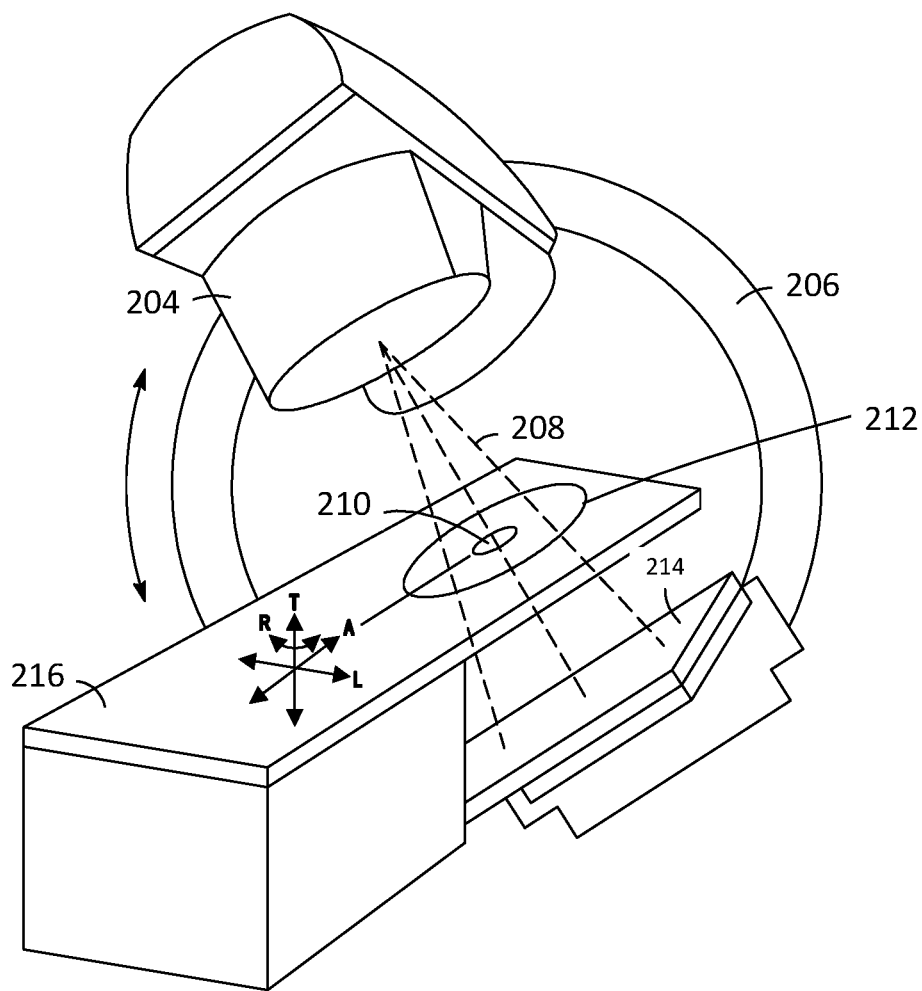
FIG. 2 illustrates an exemplary radiation therapy system that can include radiation therapy output configured to provide a therapy beam.

FIG. 2 illustrates an exemplary radiation therapy device 202 including a radiation source, such as an X-ray source or a linear accelerator, a multi-leaf collimator (not shown), a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as a multi-leaf collimator (MLC) as described in the illustrative example of FIG. 5, below.

Referring back to FIG. 2, a patient can be positioned in a region 212, using a table or couch 216 to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is in the treatment area. In an embodiment, gantry 206 may be continuously rotatable around couch 216 when the couch 216 is in the treatment area. In another embodiment, gantry 206 may rotate to a predetermined position when the couch 216 is in the treatment area. For example, the gantry 206 can be configured to rotate the therapy output 204 around an axis ("A"). The couch 216 can be moved independently of the gantry 206 and the therapy output 204, rotating about the transverse axis ("T") indicated by "R", and translating parallel to the lateral axis ("L"), the transverse axis ("T"), and the remaining axis ("A"). A controller (not shown) communicatively connected to the therapy device 202 may control the couch 216 movements or rotations in order to properly position the patient in or out of the radiation beam 208 position according to a radiation therapy treatment plan. As both the couch 216 and the gantry 206 are independently moveable from one another in multiple degrees of freedom, the patient may be positioned such that the radiation beam 208 precisely can target the tumor.

The coordinate system (including axes A, T, and L) shown in FIG. 2 can have an origin located at an isocenter 210. The isocenter can be defined as a location where the radiation therapy beam 208 intersects the origin of a coordinate axis, such as to deliver a prescribed radiation dose to a location on or within a patient. For example, the isocenter 210 can be defined as a location where the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source 204, and in an example, the imaging detector 214 can be located within a field of the therapy beam 208.

The imaging detector 214 can be mounted on the gantry 206 preferably opposite the radiation therapy output 204, such as to maintain alignment with the therapy beam 208, in which case the imaging detector 214 rotates about the rotational axis as the gantry 206 rotates. In an embodiment, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiotherapy device 202 may be integrated within system 202 or remote from it.

In an illustrative example, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus is reduced or avoided.

Figure 3:
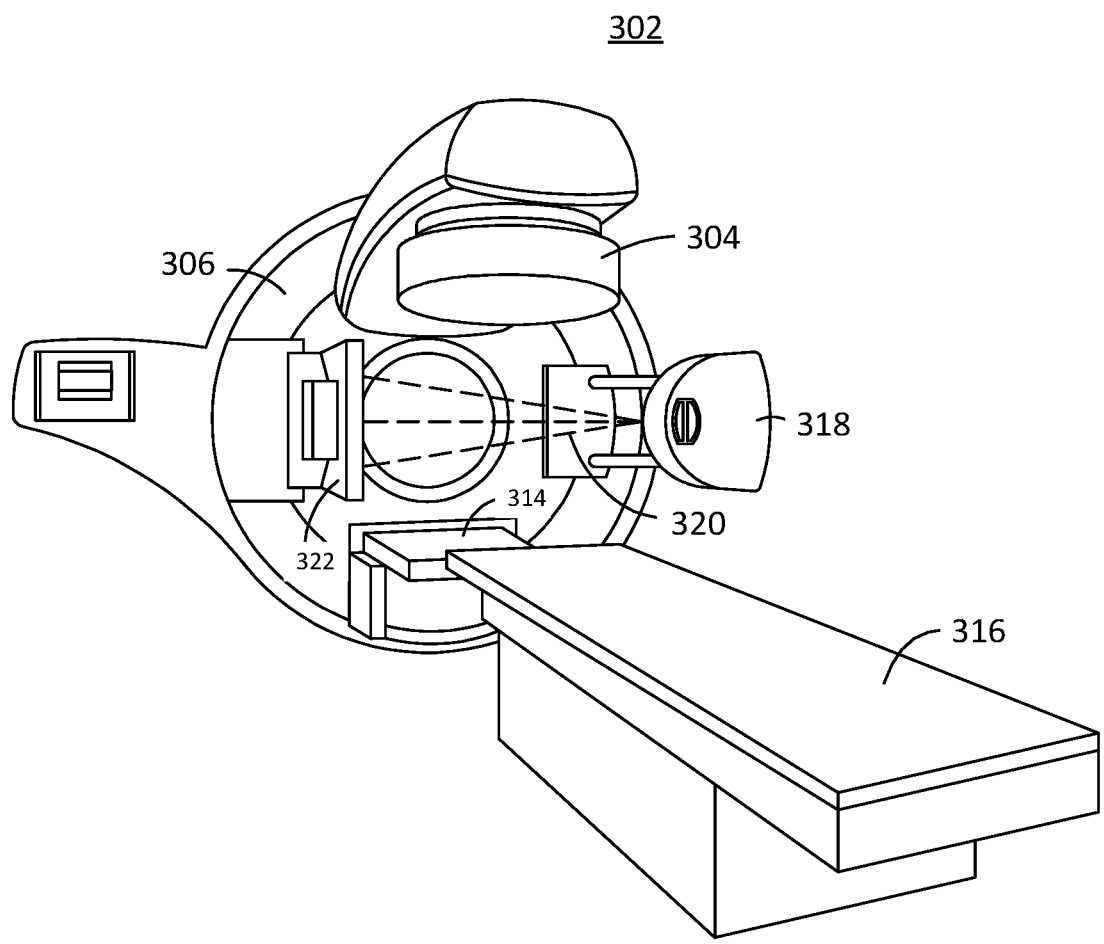
FIG. 3 illustrates an exemplary system including a combined radiation therapy system and an imaging system, such as a computed tomography (CT) imaging system.

FIG. 3 illustrates an exemplary radiation therapy device 302 that may include combining a linear accelerator and an imaging system, such as a computed tomography (CT) imaging system. The CT imaging system can include an imaging X-ray source 318, such as an X-ray source providing X-ray energy in a kiloelectron-Volt (keV) energy range. The imaging X-ray source 318 can provide a fan-shaped and/or a conical beam 320 directed to an imaging detector 322, such as a flat panel detector. The radiation therapy system 302 can be similar to the system 302 described in relation to FIG. 2, such as including a radiation therapy output 304, a gantry 306, a platform 316, and another flat panel detector 314. The X-ray source 318 can provide a comparatively-lower-energy beam for imaging than for therapy.

In the illustrative example of FIG. 3, the radiation therapy output 304 and the X-ray source 318 can be mounted on the same rotating gantry 306, rotationally-separated from each other by 90 degrees. In another example, two or more X-ray sources can be mounted along the circumference of the gantry 306, such as each having its own detector arrangement to provide multiple angles of diagnostic imaging concurrently. Similarly, multiple radiation therapy outputs 304 can be provided.

Figure 4:
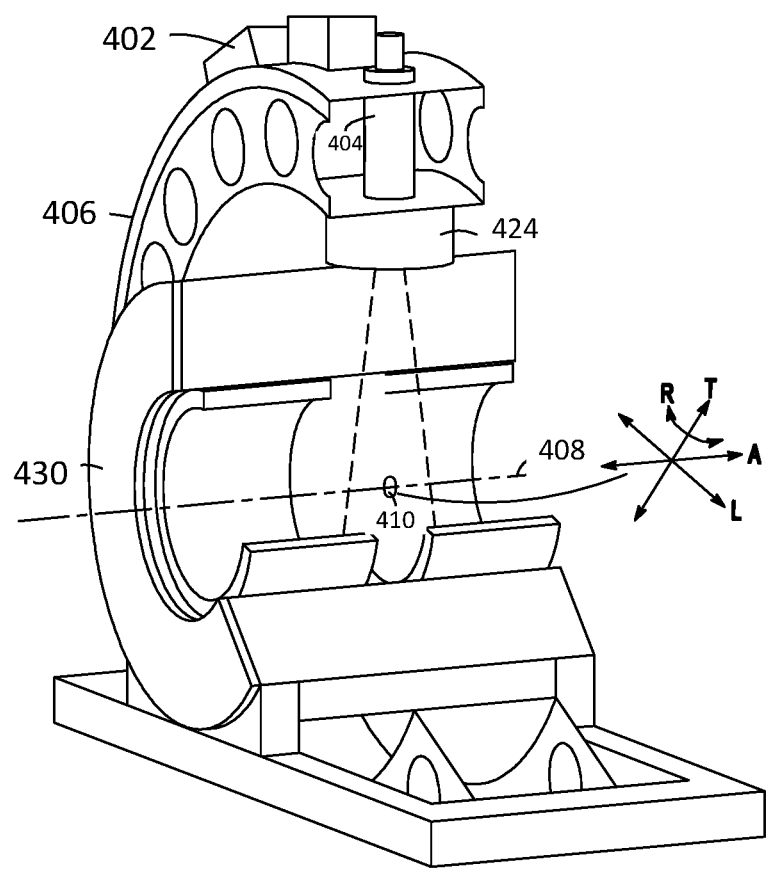
FIG. 4 illustrates a partially cut-away view of an exemplary system including a combined radiation therapy system and an imaging system, such as a nuclear magnetic resonance (MR) imaging system.

FIG. 4 depicts an exemplary radiation therapy system 400 that can include combining a radiation therapy device 402 and an imaging system, such as a nuclear magnetic resonance (MR) imaging system 430 (known in the art as a MR-Linac) consistent with the disclosed embodiments. As shown, system 400 may include a couch (not shown), an image acquisition device 430, and a radiation delivery device 424. System 400 delivers radiation therapy to a patient in accordance with a radiotherapy treatment plan. In some embodiments, image acquisition device 430 may correspond to image acquisition device 32 in FIG. 1 that may acquire origin images of a first modality (e.g., CT or MRI images).

Couch (not shown) may support a patient during a treatment session. In some implementations, couch may move along a horizontal, translation axis (labelled "A"), such that couch can move the patient into and/or out of system 400. The couch may also rotate around a central vertical axis of rotation, transverse to the translation axis. To allow such movement or rotation, couch may have motors (not shown) enabling the couch to move in various directions and to rotate along various axes. A controller (not shown) may control these movements or rotations in order to properly position the patient according to a treatment plan.

In some embodiments, image acquisition device 430 may include an MRI machine used to acquire 2D or 3D MRI images of the patient before, during, and/or after a treatment session. Image acquisition device 430 may include a magnet for generating a primary magnetic field for magnetic resonance imaging. In some embodiments, the one or more coils in the magnet may be spaced such that a central window of the magnet is free of coils to allow access of the treatment beam from source 404. In other embodiments, the coils in magnet may be thin enough or of a reduced density such that they are substantially transparent to radiation of the wavelength generated by radiotherapy device 400. Image acquisition device 430 may also include one or more shielding coils, which may generate a magnetic field outside of the magnet of approximately equal magnitude and opposite polarity in order to cancel or reduce any magnetic field outside of magnet.

In some embodiments, image acquisition device 430 may be an imaging device other than an MRI, such as an X-ray, a CT, a CBCT, a spiral CT, a PET, a SPECT, an optical tomography, a fluorescence imaging, ultrasound imaging, or radiotherapy portal imaging device, etc. As would be recognized by one of ordinary skill in the art, the above description of image acquisition device 430 concerns certain embodiments and is not intended to be limiting.

Radiotherapy device 400 may include the source of radiation 404, such as an X-ray source or a linear accelerator, and a multi-leaf collimator (MLC). Radiotherapy device gantry 406 may be mounted on a chassis. One or more chassis motors (not shown) may rotate chassis around the couch when the couch is inserted into the treatment area through axis "A". In an embodiment, chassis may be continuously rotatable around the couch, when the couch is inserted into the treatment area. The chassis may also have an attached radiation detector (not shown), preferably located opposite to radiation source 404 and with the rotational axis of the chassis positioned between radiation source 404 and the detector (not shown). Further, device 400 may include control circuitry (not shown) used to control, for example, one or more of the patient couch, image acquisition device 430, and radiotherapy output 424. The control circuitry of radiotherapy device 400 may be integrated within system or remote from it, and is functionally represented by the user interface 36 shown in FIG. 1.

FIG. 2, FIG. 3, and FIG. 4 illustrate generally examples of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient.

Figure 5:
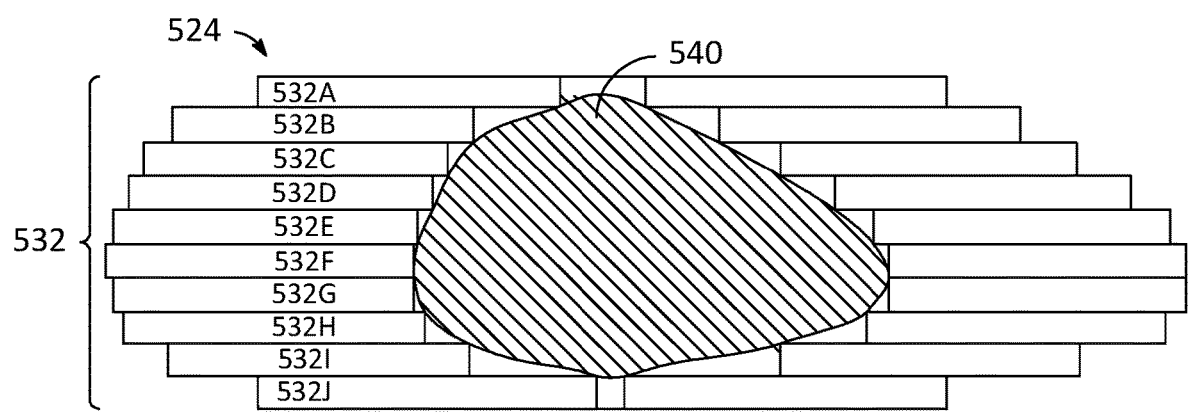
FIG. 5 illustrates an exemplary collimator configuration for shaping, directing, or modulating an intensity of a radiation therapy beam.

As discussed above, radiation therapy devices described by FIG. 2, FIG. 3, and FIG. 4 can include a multi-leaf collimator for shaping, directing, or modulating an intensity of a radiation therapy beam to the specified target locus within the patient. FIG. 5 illustrates an exemplary multi-leaf collimator (MLC) 532 that includes leaves 532A through 532J that can be automatically positioned to define an aperture approximating a tumor cross section or projection 540. The leaves 532A through 532J permit modulation of the radiation therapy beam. The leaves 532A through 532J can be made of a material specified to attenuate or block the radiation beam in regions other than the aperture, in accordance with the radiation treatment plan. For example, the leaves 532A through 532J can include metallic plates or leaves, such as comprising tungsten, with a long axis of the leaves and the leaves' ends oriented parallel to the beam direction, and having the leaves' motion orthogonal to the beam direction. A "state" of the MLC 532 can be adjusted adaptively during a course of radiation therapy treatment, such as to establish a therapy beam that better approximates a shape or location of the tumor 540 or other target locus.

Figure 6:
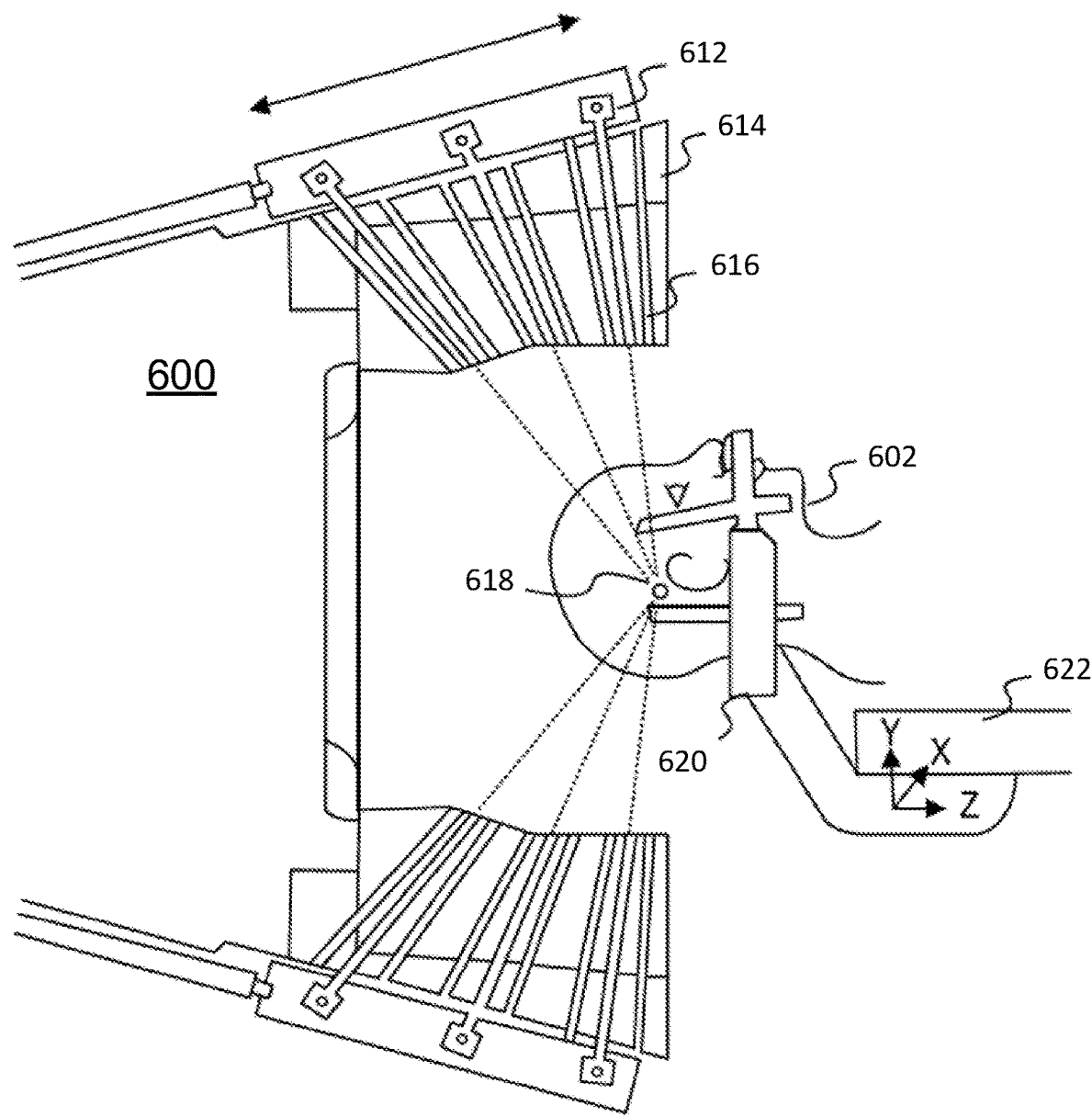
FIG. 6 illustrates an exemplary Gamma Knife radiation therapy system.

FIG. 6 illustrates an example of another type of radiotherapy device 600 (e.g., a Leksell Gamma Knife), according to some embodiments of the present disclosure. In a radiotherapy treatment session, a patient 602 may wear a coordinate frame 620 to keep stable the patient's body part (e.g., the head) undergoing surgery or radiotherapy. Coordinate frame 620 and a patient positioning system 622 may establish a spatial coordinate system, which may be used while imaging a patient or during radiation surgery. Radiotherapy device 600 may include a protective housing 614 to enclose a plurality of radiation sources 612. Radiation sources 612 may generate a plurality of millimeter-width radiation beams (e.g., beamlets) through beam channels 616. The plurality of radiation beams may be configured to focus on an isocenter 618 from different directions. While each individual radiation beam may have a relatively low intensity, isocenter 618 may receive a relatively high level of radiation when multiple doses from different radiation beams accumulate at isocenter 618. In certain embodiments, isocenter 618 may correspond to a target under surgery or treatment, such as a tumor.

Figure 7:
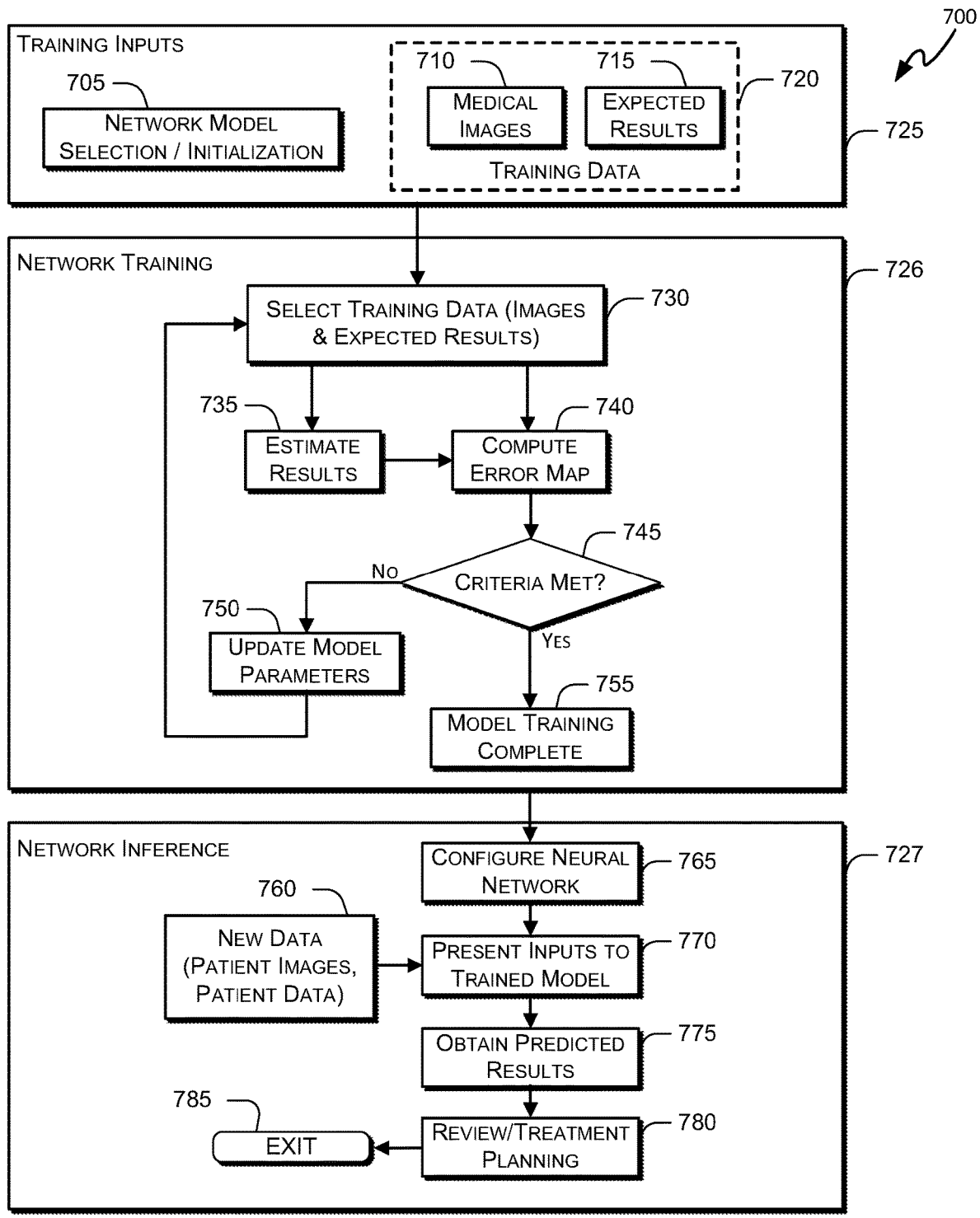
FIG. 7 illustrates a comprehensive flow diagram for embodiments of the system of the present invention.

FIG. 7 illustrates an overview of a flow diagram 700 for an embodiment of the present invention, including three phases: a training preparation phase 725, a network training phase 726, and a network inference phase 727.

In the training preparation phase 725, training inputs 720 are prepared and processed for use in training the neural network component (FIG. 1, 47). A network model is selected 705 for use in training; such model selection may include, for example, identification of a deep convolutional neural network architecture and appropriate processing layer configuration (as discussed in more detail below in regards to FIG. 8 as an example embodiment). The neural network component model (FIG. 1, 47) is initialized with an initial layer configuration, an initial connection configuration, a set of weights, and a set of biases. In addition to medical images 710 and expected results (also known to those of skill in the relevant arts as "ground truth" data) 715, other parameters (as described more fully below) may be specified for input as training data 720. In an embodiment, training data 720 may also include data for actual patients or test subjects. In another embodiment, training data 720 may be synthetically created, e.g. computer generated images based upon theoretically possible situations or devised for purposes of model testing.

In one embodiment and configuration of the neural network component model (FIG. 1, 47), input patient data corresponds to 3D information while output data from the network corresponds to 2D medical images (or image function), such as axial sections of a 3D medical image or structure. This embodiment can be optimized to interoperate with deep learning networks that operate on 2D images. In one embodiment, training data 720 may include both training data for patients and testing data for patients that are disjoint sets of the entire training data collection 720. This configuration improves accuracy testing of network iteration convergence during the training phase that follows.

In various embodiments, the preparation phase 725 includes resampling all imaging data in the training data 720 to a common grid size and grid spacing, with anatomy and dose aligned and anatomy structure centered in an axial view of the patient image. Image intensities can be resampled and inserted into channels corresponding to the output images (e.g., the RGB channels). Then, dose values can be resampled to common scale across all patients in the training data 720 to improve learning performance and convergence based on training data furnished to the network. Before such training data preparation, the training data 720 comprises medical (patient) images, image functions associated with the patient images, patient anatomy structures, and patient dose distribution, in one embodiment, oriented and registered together in a common coordinate frame. After data preparation, training data and testing data represent patient images and corresponding doses comprising the ground truth data.

The network training phase 726 commences with training data 720 being presented to the configured and initialized neural network model from step 705 (with no input dose specified). The neural network component (FIG. 1, 47) estimates results 735 from the patient image data and produces estimated results, for example, a fluence map or dose map. A comparison is then made between the estimated results from step 735 and the expected results 715 corresponding to the medical images data 710, and an error ("training error") map is generated based on differences between the expected results 715 and the estimated results 735. The error map is compared to evaluation criteria 745. For example, a loss function such as a mean absolute error function (MAE, described in more depth below) can be used to determine whether error criteria are met. If the errors do not satisfy the error threshold criterion, the model parameters of the neural network (FIG. 1, 47) (e.g., weights and biases) are updated 750, e.g. to minimize error according to a learning algorithm (e.g. a regularized gradient descent optimization approach), and the training data is re-presented 730 to the neural network (FIG. 1, 47) with the neural network's newly-assigned model parameters.

In one embodiment, determining whether criteria are met 745 includes presenting one or more test patient images that are different from the training images (but have no input dose specified) to the network model as currently configured to generate an estimate of the patient dose for such test patient images. The resulting dose estimate can then be compared with the ground truth/expected dose to assess the quality of the network parameter model. The differences between the expected dose and the estimated dose for this test data is the "test error." In any event, iteration from step 750 to step 730, to steps 735 and 740, to step 745 continues until the error threshold criterion is met, whereupon the training process 725 concludes 755, with a trained neural network component model ready for use with real patient images and data (FIG. 1, 45, 46).

Once trained, the neural network component model (FIG. 1, 47) may be stored in a memory (e.g., FIG. 1, 16), within non-transitory memory of the network component (FIG. 1, 47) or in a database (e.g. FIG. 1, 24). The trained network model may then be used in the network inference steps 727 to compute a useful output (e.g. a fluence map or dosage map) when presented with patient data (FIG. 1, 45, 46) for whom a radiation treatment plan is desired. The trained neural network is configured 765, for example, by loading stored weights and biases for the particular trained network configuration. Patient data inputs are presented to the trained and configured neural network component (FIG. 1, 47) to obtain predicted results. In a preferred embodiment, predicted results comprise one of fluence map information and dose map information; the fluence map or dose map information may then be used to complete a radiation treatment plan for the patient. Thus, for the patient of interest, patient images and/or data 760 are presented to the trained and configured neural network model 770 to produce the predicted results 775. In a further embodiment, the predicted results are in turn processed for use by a treatment planning system 780, such as for generation of dose-volume histograms (DVHs) for use in a treatment planning system (for example, in the MONACO® system by Elekta AB of Stockholm, Sweden).

Embodiments of the present invention provide for fluence and dose map calculations involving internal as well as external radiation sources. Embodiments include those providing calculations for internal brachytherapy applications. Brachytherapy generally involves the placement of a radiation source directly at a tumor site. Calculations to determine the optimal treatment profiles often require complex calculations and estimates utilizing the Linear Boltzman Transport Equation in various optimization routines. By training a neural network of the present invention to identify fluence maps from idealized input data (e.g. patient images and desired results), brachytherapy applications can be supported.

In various embodiments of the present invention, brachytherapy planning proceeds from a starting point similar to external beam therapy (a planning CT or MR image with target and OARs delineated, and a target prescription and OAR constraints) to achieve a dose distribution that satisfies the plan criteria. Therefore, in various embodiments, the application of deep learning to predict the brachytherapy dose distribution would be analogous to the external beam distribution prediction. For both therapies, the network model learns the mapping from the structures in images to dose maps, and uses it to predict a dose map for a new patient. That learned mapping ignores the mechanistic details of therapy administration.

Additional aspects of the present invention regarding brachytherapy provide for use of a Deep Convolutional Neural Network (DCNN) to provide estimated doses at varying times during decay of the applied radiation source. In such aspects, time of sampling is an additional parameter in the training set and 4-D analysis (involving dwell time or treatment time) may provide for cumulative dose based on the particular radiation source(s). The predicted results of these embodiments assist with determining placement of the radiation sources in the patent's target treatment area, the radiation dose intensity to be delivered to the treatment target, and the duration of dose delivery over time.

In another embodiment, real-time MRI images may be used in conjunction with brachytherapy. MRI devices provide excellent soft-tissue contrast and precise imaging of the tumor and surrounding organs. This allows for improved accuracy of brachytherapy source implantation, improved delineation of targets and organs-at-risk (OAR), and improved dose prescription. The real-time MRI images from an MRI device (e.g., where MRI device and brachytherapy device are operating simultaneously) may provide real-time visualization for the proper placement of a brachytherapy applicator and brachytherapy radioactive source to (1) avoid perforations and (2) guide the source to a target in order to provide a brachytherapy treatment. Another advantage of MR over CT-based images is MR can provide more accurate target contours than CT, which allows for better delineation of target structures and for a higher degree of dose optimization. Although MRI improves the visibility of the target structures compared to CT, target contouring still provides uncertainties related to image-guided procedures. Being able to track both the source and applicator by using MRI would allow for 1) implant verification, 2) source dwell position measurements (e.g., typically 20 source positions at 5 mm distance and a dwell time of 0.5 second per source position), and 3) does planning with real radiation dose distribution in the patient. In a further embodiment, functional MRI (fMRI) can be used for prostate brachytherapy. Functional MRI can improve the identification of intra-prostatic lesions, which is of particular interest for salvage prostate brachytherapy and for subvolume boosting.

The input data may include medical images. The input data may include at least one of anatomical data and planning metaparameters. In some aspects, planning metaparameters may include device constraints, diagnosis information, and other information about the planned course of radiation therapy. Device constraints may include beam gantry angles, beamlet vectors, and similar restrictions on radiation delivery.

Figure 8:
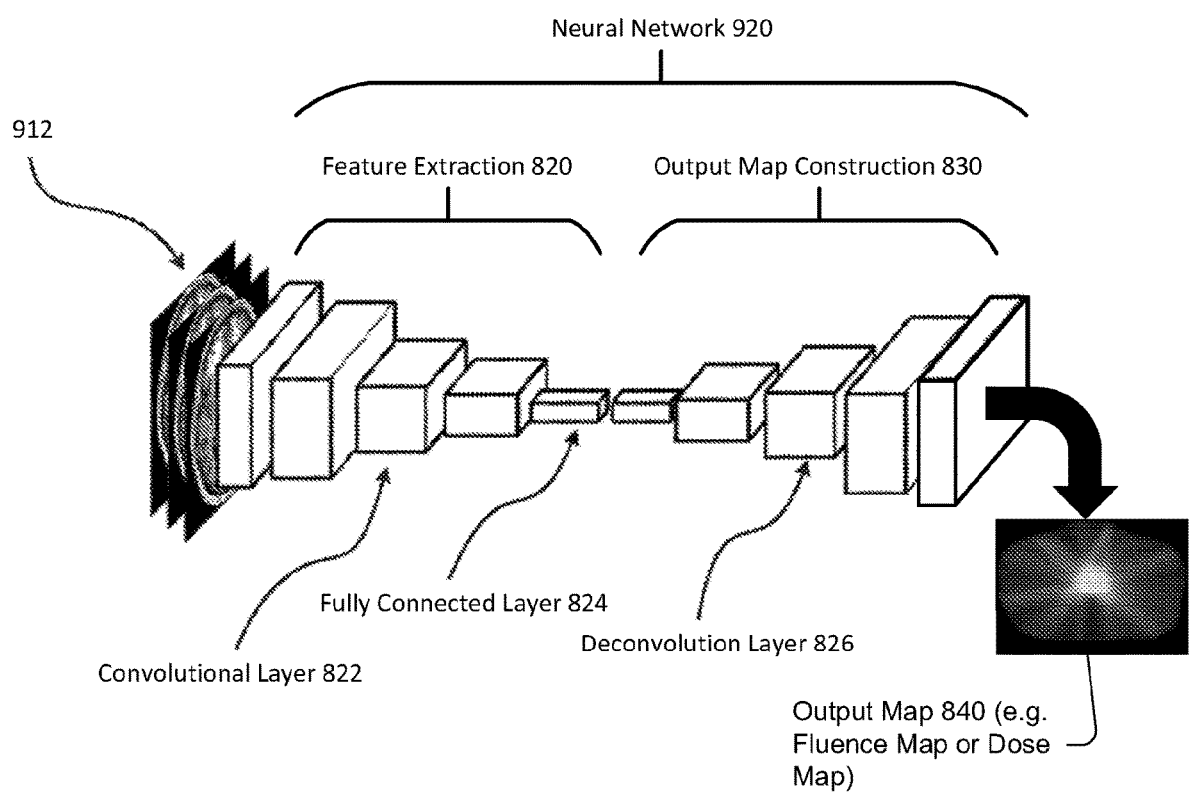
FIG. 8 illustrates an exemplary deep convolutional neural network (DCNN) model for output map generation, according to some embodiments of the present disclosure.
Figure 9:
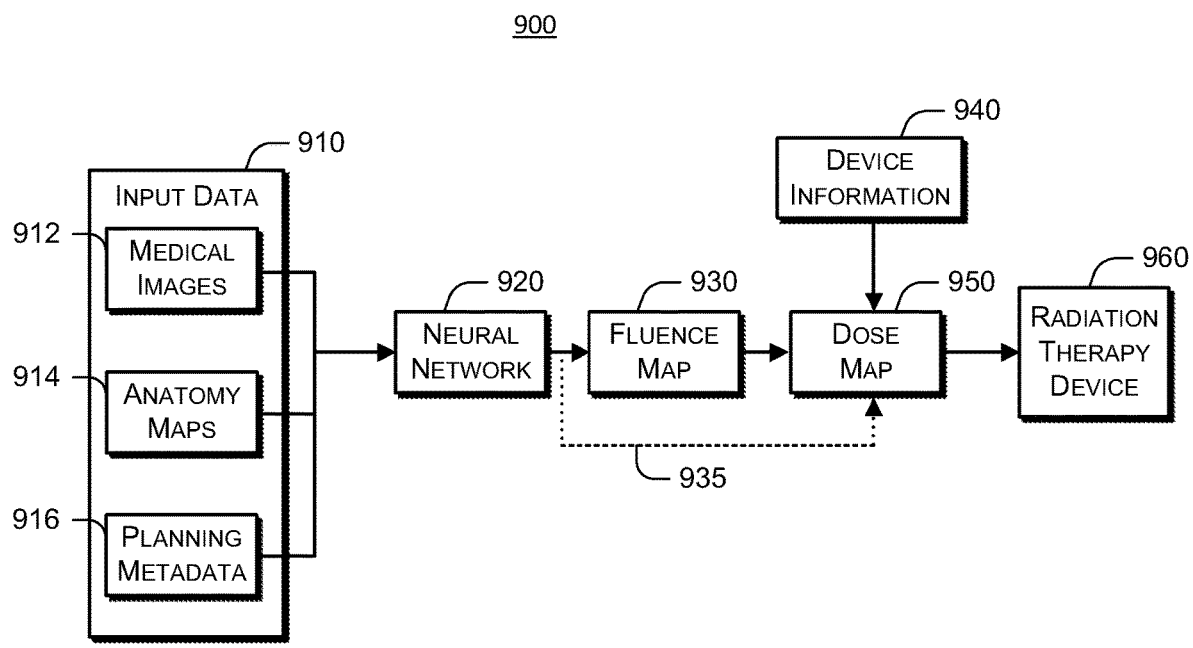
FIG. 9 depicts generation and use of an output map in an exemplary radiotherapy system.

As depicted in FIG. 9, embodiments of systems and methods of the present invention may be used to generate a fluence map 930 and dose map 950 from input data. For example, system 900 may be configured to generate a dose map 950 for use with radiation therapy device 960 from input data 910. Dose map 950 may depict the localized deposition of energy in the patient subject to the constraints imposed by radiation device 160. Fluence map 930 may typically differ from dose map 950, and the disclosed systems and methods may be configured to reduce this difference. In some aspects, as depicted in alternative path 935, system 900 may be configured to use neural network 920 to generate dose map 950 directly from input data 910. Input data 910 may comprise medical images 912, anatomy maps 914, and planning metadata 916. The medical images 912 may have been acquired from a patient using an imaging modality. The anatomy maps may indicate a set of defined targets and sensitive organs of the patient. In some aspects, the defined targets may include tumors. Input data 910 may be provided to neural network 920. As described more completely below and above in regards to FIG. 7, neural network 920 may be trained to generate fluence maps 930 (and, alternatively dose maps 950) from input data 910. Neural network 920 may comprise a convolutional neural network, and in some aspects, fluence map 930 may comprise an output of neural network 920. The neural network 920 shown in FIG. 9 may comprise the same or a similar architecture to the neural network component 47 shown in FIG. 1, and the neural network 920 shown in FIG. 8.

Additionally, the neural network 920 of FIG. 9 may include a deep convolutional neural network (DCNN). The architecture of a DCNN model includes a stack of distinct layers that transform the input into the output. Examples of the different layers may include one or more convolutional layers, non-linear operator layers (such as rectified linear units (ReLu) functions, sigmoid functions, or hyperbolic tangent functions), pooling or subsampling layers, fully connected layers, final loss layers, deconvolution layers, unpooling or upsampling layers, pixel-wise predicting layers, and/or copy and crop operator layers. Each layer may connect one upstream layer and one downstream layer. The input may be considered as an input layer, and the output may be considered as the final output layer.

To increase the performance and learning capabilities of DCNN models, the number of different layers can be selectively increased. The number of intermediate distinct layers from the input layer to the output layer can become very large, thereby increasing the complexity of the architecture of the DCNN model. The present disclosure employs the powerful learning DCNN models, to generate fluence and/or output maps. Consistent with the disclosed embodiments, system 900 may be configured to generate fluence maps 930 or dose maps 950 using a trained DCNN model (implemented in neural network 920) that receives input data 910. Advantageously, the DCNN model for generation of fluence maps and dose maps in the embodiments of the present disclosure allows for automatic generation of such maps without the need of manual feature extraction.

As used herein, a DCNN model used by the disclosed generation method may refer to any neural network model formulated, adapted, or modified based on a framework of convolutional neural network. For example, a DCNN model used for generation of fluence and/or dose maps in embodiments of the present disclosure may selectively include intermediate layers between the input and output layers, such as one or more convolutional layers, non-linear operator layers, pooling or subsampling layers, fully connected layers, final loss layers, deconvolution layers, and/or unpooling or upsampling layers.

The disclosed systems and methods for generating output maps generally include two stages: a training stage that "trains" or "learns" a DCNN model using training datasets, and a prediction or inference stage in which the trained DCNN model uses the training datasets and input data to generate output maps. As mentioned above, the aforementioned training stages generally correlates with the network training 726 as depicted in FIG. 7. As used herein, "training" a DCNN model refers to determining one or more parameters of at least one layer in the DCNN model. For example, a convolutional layer of a DCNN model may include at least one filter or kernel. One or more parameters, such as kernel weights, size, shape, and structure, of the at least one filter may be determined by e.g., a back-propagation-based training process.

The aforementioned prediction stage generally correlates with network inference 727 as depicted in FIG. 7. As used with respect to the embodiment described herein, "predicting" from a DCNN model refers to generating a fluence and/or dose map using medical images 912 including, both 2D and 3D fluence and/or dose maps from any type of imaging modality.

DCNN Model for Output Map Generation

FIG. 8 illustrates exemplary neural network 920 which implements a deep convolutional neural network architecture for output map generation (e.g. generation of fluence maps and/or dose maps), according to some embodiments of the present disclosure. Neural network 920 may comprise a deep convolutional neural network. As shown in FIG. 8, neural network 920 may receive medical images 912 acquired using one or more first imaging modalities as input. Medical images, as used herein, may include without limitation the contents of input data (FIG. 9, 910), including medical images 912, anatomy maps 914, and planning metadata 916. Neural network 920 may produce output 840 corresponding to a fluence map or dose map. Output 840 may concern the same subject matter as one of the input medical images. For example, when medical images 912 comprises a stack of adjacent images, output 840 may concern the same subject matter as one of the images in the middle of the stack 912. For example, when medical images 912 comprises an odd number of images, output 840 may concern the same subject matter as the middle image of the stack. Alternatively, when medical images 912 comprises an even number of images, output 840 may concern the same subject matter as one of the two middle images of the stack.

As shown in FIG. 8, an embodiment of a neural network 920 of the present invention may generally include two portions: a first feature extraction portion 820 and a second output map construction portion 830. Feature extraction portion 820 may extract one or more features of medical images 912. Feature extraction portion 820 uses a deep convolutional neural network approach to receive medical images 912 and to output at least one feature vector or matrix representing the features of the input stack. Thus feature extraction portion 820 may extract features at different scales and different complexity levels, each layer of feature extraction portion 820 receiving as its input the latent representation of the preceding layer. Output map construction portion 830 may use the output of feature extraction portion 820 to generate output 840, which as mentioned previously, may comprise a fluence map or dose map. The second portion may gradually reconstruct the output map from coarse resolution to fine, until the desired image resolution or image size is achieved.

In some embodiments, neural network 920 may be configured with direct connections from the output of a layer in feature extraction portion 820 to the input of a layer in output map construction 830. In some aspects, such connections may only be from the output of the final layer of feature extraction portion 820 to the input of the initial layer of output map construction 830. In various aspects, neural network 920 may be configured with one or more additional connections between feature extraction portion 820 and output map construction 830. These connections may involve non-final layers of feature extraction portion 820 and non-final layers of output map construction 830, final layers of feature extraction portion 820 and non-final layers of output map construction 830, and/or non-final layers of feature extraction portion 820 and final layers of output map construction 830.

In some embodiments, feature extraction portion 820 and output map construction 830 may be trained together. For example, the parameters of feature extraction portion 820 and output map construction 830 may be updated together during each iteration of model training. In various embodiments, feature extraction portion 820 and output map construction 830 may be trained separately. For example, feature extraction portion 820 may comprise a known model, such as a VGG image classification model, and only the parameters of output map construction 830 may be updated during training.

Advantageously, the accuracy of neural network may 920 increase when medical images 912 comprises a stack of adjacent 2D images that contain dependent structure information. Neural network 920 may be configured to use such a stack of adjacent 2D images both when training and when generating output maps in the form of fluence maps or dose maps. As used herein, the dependent structure information may refer to a spatially dependent relationship between the anatomical structures shown in the stack of adjacent 2D images along the axis orthogonal to the anatomical plane of the 2D images. As a non-limiting example, the shape and type of an anatomical structure represented by a first set of pixels in a first image of the stack may also be represented by a second set of pixels in a second image adjacent to the first image. This is because the spatial neighboring of the first and second images along the axis orthogonal to the anatomical plane allows for some dependency or continuity of the anatomical structures shown in these images. Therefore, the shape, size, and/or type of an anatomical structure in one image may provide information of the shape, size, and/or type of the anatomical structure in another adjacent image along the same plane. The effect of dependent structure information may depend on the number of adjacent images in the stack, the anatomical structures depicted in medical images 912, and/or the imaging modality used for obtaining the images.

Various components and features of neural network 920 used in the embodiments of the present disclosure are described in detail below.

DCNN for Feature Extraction

In some embodiments, feature extraction portion 820 of the neural network 920 includes an input layer, e.g., medical images 912. In some embodiments, medical images 912 may comprise multiple images. In some aspects, medical images 912 may comprise one or more sets of medical images. For example, medical images 912 may comprise one or more 3D CT images. In various aspects, medical images 912 may comprise a stack of adjacent 2D CT images. As described above, adjacent slices may provide neural network 920 with dependent structure information enabling more accurate or robust predictions.

In some embodiments, feature extraction portion 820 of the neural network 920 includes an input layer, e.g., functions of medical images 912 or functions of anatomy maps 914. In some embodiments, the patient anatomy information may be encoded in binary masks or images in which delineated structures like the radiotherapy target and nearby organs at risk are represented by a fixed pixel value and all pixels outside the structure are set to a background value. In some embodiments, the patient anatomy information may be encoded as signed distance maps in which each pixel value is equal to the shortest distance to the structure boundary, where pixels inside the structure are assigned a positive value and pixels outside the structure are assigned a negative value. In some embodiments, the patient anatomy information may be encoded as functions of the original image transformed by an algorithm to a new image in which, e.g., anatomy structure edges are emphasized. These embodiments are illustrative of what may be useful in feature extraction, and not limiting in any way.

In some embodiments, the input layer has a volume, whose spatial dimensions are determined by the width and height of the 2D images, and whose depth is determined in part by the number of images comprising medical images 912.

In some embodiments, feature extraction portion 820 of neural network 920 may include one or more convolutional layers 322. Each convolutional layer 322 may have a plurality of parameters, such as the width ("W") and height ("H") determined by the upper input layer (e.g., the size of the input of convolutional layer 322), and the number of filters or kernels ("N") in the layer and their sizes. The number of filters may be referred to as the depth of the convolutional layer. Therefore, each convolutional layer 322 may be described in terms of a 3D volume as shown in FIG. 8. The input of each convolutional layer 322 may be convolved with one filter to produce a feature map corresponding to that filter. Such convolution may be performed for each filter of each convolutional layer. The resulting feature maps may have a width and height, and may be stacked along a depth dimension, generating a 3D output. This output may comprise the input to the next convolutional layer.

In some embodiments, feature extraction portion 820 of neural network 920 may include one or more pooling layers (not shown). A pooling layer can be added between two successive convolutional layers 322 in neural network 920. A pooling layer operates independently on every depth slice of the input (e.g., a feature map from a previous convolutional layer), and reduces its spatial dimension by performing a form of non-linear down-sampling. As shown in FIG. 8, pooling layers may progressively reduce the spatial dimension of the extracted feature maps to reduce the amount of parameters and computation in the network. This may also control overfitting. The number and placement of the pooling layers may be determined based on various factors, such as the design of the convolutional network architecture, the size of the input, the size of convolutional layers 322, and/or application of neural network 920.

Various non-linear functions can be used to implement the pooling layers. For example, max pooling may be used. Max pooling may partition an image slice of the input into a set of overlapping or non-overlapping sub-regions with a predetermined stride. For each sub-region, max pooling may output the maximum, down-sampling every slice of the input along both its width and its height, while leaving the depth dimension remains unchanged. Other suitable functions may be used for implementing the pooling layers, such as average pooling or L2-norm pooling.

In various embodiments, feature extraction portion 820 of neural network 920 may include one or more additional layers. As a non-limiting example, a ReLu layer (not shown) may be selectively added after a convolutional layer to generate an intermediate activation map or feature map. The ReLu layer may increase the nonlinear properties of the predictor function and the overall of neural network 920 without affecting the respective dimensions of convolutional layers 322. Additionally, the ReLu layer may reduce or avoid saturation during a back-propagation training process.

As another non-limiting example, one or more fully connected layers 824 may be added after the convolutional layers and/or the pooling layers. A fully connected layer 824 may have a full connection with all activation maps or feature maps of the previous layer. For example, a fully connected layer 824 may take the output of the last convolutional layer or the last pooling layer as the input in vector form, and perform high-level determination and output a feature vector arranged along the depth dimension. The output vector may be referred to as an output layer. The vector may contain information of the anatomical structures in input stack of medical images 912 of neural network 920.

Convolutional Neural Network for Output Map Construction

As described above, output map construction 830 of neural network 920 may generate output map 840 using one or more features output by feature extraction portion 820. As mentioned elsewhere, output map 840 may comprise a fluence map or a dose map, and may comprise the predicted results discussed in regards to FIG. 7, 775.

As shown in FIG. 8, output map construction 830 of neural network 920 may convert a coarse output feature map (e.g., a feature vector) of feature extraction portion 820 to output map 840. Various functions may be used to implement the pixel-wise prediction layer, such as backwards upsampling or unpooling (e.g., bilinear or nonlinear interpolation), and backwards convolution (deconvolution). In some aspects, output map construction 830 of neural network 920 may comprise a mirrored version of feature extraction portion 820 of neural network 920. While feature extraction portion 820 may progressively reduce the spatial dimensions of the extracted activation maps or feature maps, output map construction portion 830 may progressively enlarge feature maps using deconvolution layers 826 and/or unpooling layers (not shown). An unpooling layer (e.g., an upsampling layer) may receive pixels in a feature map, and output a larger feature map, with the pixels of the feature map returned to their previous or original pool location, thereby generating an enlarged, yet sparse activation map or feature map. A deconvolution layer may be used to associate a single pixel of an input activation map or feature map to multiple output pixels, thereby enlarging and increasing the density of the activation map or feature map. Therefore, output map construction portion 830 may be trained and used together with feature extraction portion 820 to generate output map 840.

As would be appreciated by those skilled in the art, other suitable methods for generating output map 840 may be adapted, modified, and/or used in the embodiments of the present disclosure.

DCNN Model-Based Output Map Generation System

Figure 10:
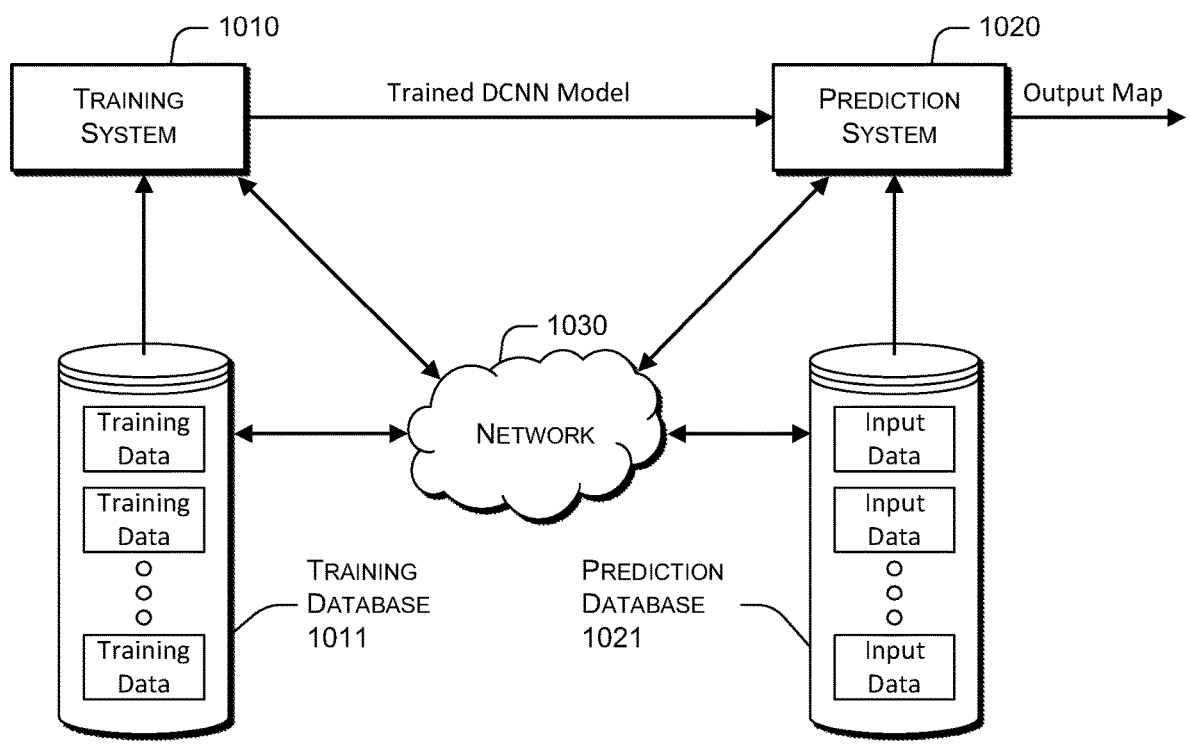
FIG. 10 illustrates an exemplary system for output map generation, according to some embodiments of the present disclosure.

FIG. 10 illustrates an exemplary embodiment of the present invention showing an output map generation system 1000 for generating output maps using at least one CNN model, according to some embodiments of the present disclosure. As shown in FIG. 10, output map generation system 1000 may include components for performing two stages, a training stage and a generation stage. To perform the training stage, output map generation system 1000 may include a training database 1011 and a training system 1010. To perform the output map generation stage, output map generation system 1000 may include a prediction system 1020 and a prediction database 1021. In some embodiments, output map generation system 1000 may include more or less of the components shown in FIG. 10. For example, when a DCNN model for output map generation is pre-trained and provided, output map generation system 1000 may only include prediction system 1020 and prediction database 1021. Output map generation system 1000 may optionally include a network 1030. In some embodiments, network 1030 may be replaced by wired data communication systems or devices.

In some embodiments, the various components of output map generation system 1000 may be located remotely from each other or in different spaces, and be connected through network 1030 as shown in FIG. 10. In some alternative embodiments, certain components of output map generation system 1000 may be located on the same site or inside one device. For example, training database 1011 may be located on site with training system 1010, or be part of training system 1010. As another example, training system 1010 and prediction system 1020 may be inside the same computer or processing device.

As shown in FIG. 10, training system 1010 may communicate with training database 1011 to receive training data. The training data stored in training database 1011 may be obtained from a medical image database, for example, a medical image database containing previously acquired medical images during radiotherapy treatment sessions. Each item of training data may include one or more medical images acquired in one or more origin imaging modalities, one or more anatomy maps, planning metadata, and corresponding predetermined output map.

In various aspects, the one or more training images may comprise medical images having a predetermined spatial relationship. In some aspects, the one or more training images may comprise a 3D medical image acquired in an origin imaging modality. System 1000 may be configured to divide the 3D medical image into one or more sequential stacks of adjacent 2D medical images. The number of adjacent 2D images in each stack may be determined based on various factors, such as the size of the 3D image, a specific framework of the CNN model, the relationship between the anatomical structures in the adjacent 2D images along an axis orthogonal to the 2D image, and/or the application of the output map generation.

In some embodiments, when the one or more training images comprise a stack of medical images in one or more origin imaging modalities, the output map may correspond spatially to a middle image of the stack (e.g., the central image for a stack with an odd number of images, and one of the two middle images for a stack with an even number of images).

Consistent with the disclosed embodiments, the one or more training images may be acquired using various imaging modalities, including MRI, functional MRI (e.g., fMRI, DCE-MRI and diffusion MRI), CT, CBCT, Spiral CT, PET, SPECT, X-ray, optical tomography, fluorescence imaging, ultrasound imaging, and radiotherapy portal imaging, etc. In some embodiments, the one or more training images may be collected from an Oncology Information System.

In various aspects, the one or more anatomy maps may comprise segmentation information corresponding to the one or more training images. For example, the one or more anatomy maps may comprise delineations of the target volumes and normal critical organs in the one or more training images. For example, the anatomy maps may comprise labels associating pixel or voxels with anatomical structure, or predictions of the anatomical structure each pixel or voxel of the training image represents. These anatomy maps may be generated according to methods known to one of skill in the art, such as manual segmentation or atlas-based auto-segmentation. The anatomy maps may also be generated using machine learning methods.

In some aspects, the planning metadata may comprise information about the planning process. For example, the planning metadata may comprise information about a diagnosis of the patient, the type and characteristics of the radiation therapy device, or similar information. For example, planning metadata may comprise beam gantry angles, beamlet vectors, and similar information.

Training system 1010 may use the training data received from training database 1011 to train a CNN model for generating output maps in the form of fluence maps and/or dose maps. Training system 1010 may include a processor and a non-transitory computer-readable medium (discussed in detail in connection with FIG. 1). The processor may conduct the training by performing instructions of a training process stored in the computer-readable medium. Training system 1010 may additionally include input and output interfaces (discussed in detail in connection with FIG. 1) to communicate with training database 1011, network 1030, and/or a user interface (not shown). The user interface may be used for selecting training data (i.e., images in the one or more original imaging modalities and the destination imaging modality), adjusting one or more parameters of the training process (e.g., the number of adjacent image slices in each stack), selecting or modifying a framework of a DCNN model, and/or manually or semi-automatically editing images for training. Examples of the training process are described in detail with reference to FIG. 11 further below.

Consistent with some embodiments, training system 1010 may be implemented with hardware (e.g., as disclosed in FIG. 1) specially programmed by software that performs the training process (e.g., as disclosed in FIGS. 1 and 7).

Prediction system 1020 may receive at least one trained CNN model from training system 1010. Prediction system 1020 may include a processor and a non-transitory computer-readable medium (discussed in detail in connection with FIG. 1). The processor may execute instructions of an image-generation process stored in the non-transitory computer-readable medium, causing prediction system 1020 to perform operations for generating an output map. Prediction system 1020 may additionally include input and output interfaces (discussed in detail in connection with FIG. 1) to communicate with prediction database 1021, network 1030, and/or a user interface (not shown, but in one embodiment corresponding to FIG. 1, 36). The user interface may be used for selecting one or more medical images as a basis for generating an output map, initiating the generation process, outputting the output map, and/or performing further analysis based on the output map.

Figure 12:
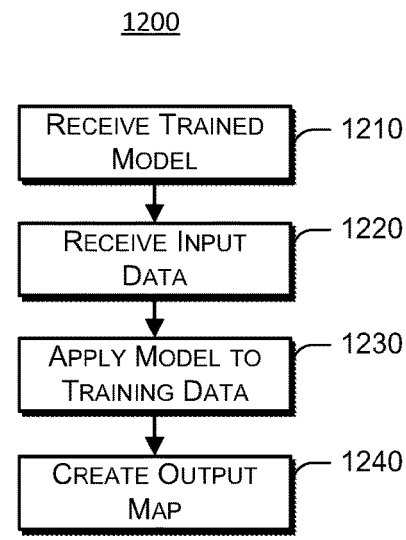
FIG. 12 depicts a flowchart illustrating an exemplary output map generation process using trained CNN models obtained through the process of FIG. 11.

Consistent with some embodiments, prediction system 1020 may be implemented with hardware (e.g., as disclosed in FIG. 1) specially programmed by software that configures prediction system 1020 to generate an output map (e.g., as disclosed in FIG. 12).

Prediction system 1020 may communicate with prediction database 1021 to receive input data. In some aspects, the input data may comprise one or more medical images. The medical images stored in prediction database 1021 may be obtained from a medical image database, which contains 2D and/or 3D images of radiotherapy treatment sessions, for example. As described herein, the medical images may comprise 3D medical images, which may be reconstructed from 2D projection images acquired by medical imaging devices, such as image acquisition device FIG. 1, 32.

Consistent with the disclosed embodiments, the medical images may be acquired using various imaging modalities, including MRI, functional MRI (e.g., fMRI, DCE-MRI and diffusion MRI), CT, CBCT, Spiral CT, PET, SPECT, X-ray, optical tomography, fluorescence imaging, ultrasound imaging, and radiotherapy portal imaging, etc. In some embodiments, prediction database 1021 may be an integrated part of prediction system 1020, or located on the same site of prediction system 1020, such as in a radiotherapy treatment room.

In some aspects, the input data may further comprise anatomy maps. As described above, the one or more anatomy maps may comprise segmentation information corresponding to the one or more medical images. For example, the one or more anatomy maps may comprise delineations of the target volumes and normal critical organs in the one or more medical images. In some aspects, the input data may further comprise planning metadata. For example, the planning metadata may comprise information about a diagnosis of the patient, the type and characteristics of the radiation therapy device, or similar information. For example, planning metadata may comprise beam gantry angles, beamlet vectors, and similar information.

Prediction system 1020 may use at least one trained CNN model received from training system 1010 to generate an output map. When this generation is completed, prediction system 1020 may output the output map. The output map may be displayed in the user interface, and/or stored in prediction database 1021 for further use in treatment planning. In some embodiments, the output map may be automatically stored in training database 1011. For example, the output map may be associated with the received medical images, the received anatomical maps, and the planning metadata. One or more of these associated items may be stored as training data in training database 1011.

Network 1030 may provide connections between any of the above described components in image segmentation system 1000. For example, network 1030 may be a local area network (LAN), a wireless network, a cloud computing environment (e.g., software as a service, platform as a service, infrastructure as a service), a client-server, and a wide area network (WAN), among others.

Exemplary DCNN Model Training Processes

Figure 11:
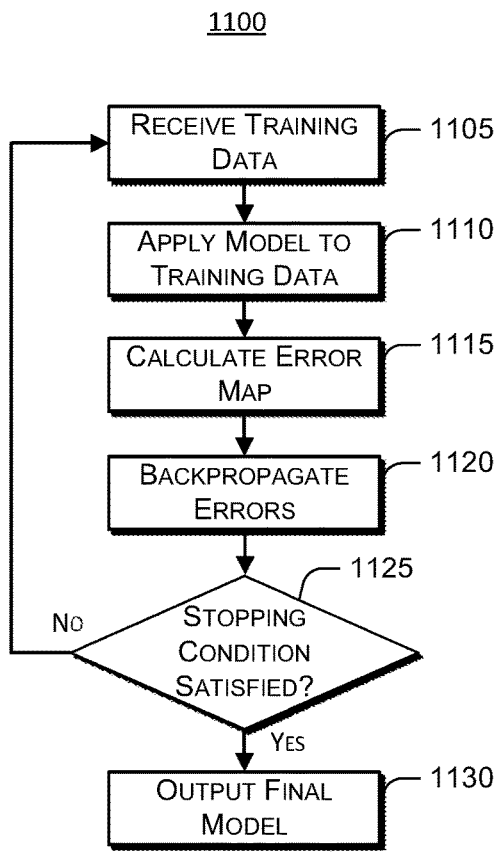
FIG. 11 depicts a flowchart illustrating an exemplary training process for training a DCNN model.

Exemplary training processes performed by the disclosed systems and methods of output map generation are described above in regards to FIG. 7 and in additional detail below with references to FIG. 11, which depicts a flowchart illustrating an exemplary training process 1100 for training a DCNN model, according to some embodiments of the present disclosure. In some embodiments, training process 1100 may be performed by training system 1010.

Training process 1100 may start when training system 1010 receives training data (Step 1105). As described above, training data may include at least one or more medical images acquired using one or more imaging modalities and a corresponding output map. The medical images may be 3D or 2D medical images. For example, the medical images may include CT images of an anatomical area of a patient, such as a head, torso, abdomen, and/or limbs. In some embodiments, the CT images may be 3D CT images, or one or more stacks of 2D images. The output map may comprise a fluence map or dose map. In some aspects, training data may also include one or more anatomy maps. In various aspects, training data may also include planning metadata.

In some embodiments, training system 1010 may be configured to preprocess the training data. For example, when the one or more medical images comprise one or more 3D medical images, training system 1010 may be configured to generate one or more stacks of adjacent 2D images from the one or more 3D medical images. The one or more stacks may constitute substantially the whole 3D training image. The one or more stacks may comprise overlapping images (e.g., the same or substantially similar images may be present in more than one of the stacks). As described above, a stack of adjacent 2D medical images may collectively comprise dependent structure information along an axis orthogonal to the anatomical plane. When the output map comprises a 3D medical image, training system 1010 may be configured to generate a 2D output map from the 3D output map. When the one or more anatomy maps comprises one or more 3D images, training system 1010 may be configured to generate one or more stacks of adjacent 2D anatomy maps from the one or more 3D anatomy maps. The 2D anatomy maps in the one or more stacks of adjacent 2D anatomy maps may correspond to 2D medical images in the one or more stacks of adjacent 2D medical images. In some embodiments, training system 1010 may be configured to use the one or more stacks of medical images and corresponding output map collectively as one batch of training data to train a DCNN model. In various embodiments, training system 1010 may be configured to also use the one or more stacks of adjacent 2D anatomy maps, and/or the planning metadata.

In some embodiments, the one or more stacks of medical images may be along a selected plane from the three anatomical planes, such as the axial plane, sagittal plane, or coronal plane. In such instances, process 1100 may output a trained DCNN model for this selected plane (e.g., for generating output maps from medical images along this selected plane). In some embodiments, process 1100 may be repeated to output three different DCNN models trained for generating output maps along the three anatomical planes respectively.

In other embodiments, the one or more stacks of adjacent 2D images may be along two or more selected anatomical planes. Process 1100 may be performed to output one trained DCNN model that can be used for generating output maps along any one of the two or more selected anatomical planes. In other embodiments, the one or more stacks of adjacent 2D images may be along any of the three anatomical planes, e.g., at least one stack of adjacent 2D images is selected for each anatomical plane. Process 1100 may be performed to obtain one trained CNN model that can be used for generating output maps along any of the three anatomical planes.

In such instances, the DCNN model is trained using combined stacks of adjacent 2D images along all three anatomical planes.

Steps 1105 through 1125 may be performed iteratively to train a DCNN model until the DCNN model outputs satisfactory output maps. The number of iterations may be determined by various stopping criteria. In some embodiments, a maximum number of iterations may be used. At each iteration, a new batch of training data may be received, or generated from previously received data. The new batch of training data may be used for training the DCNN model until the maximum number of iterations is reached. Additionally or alternatively, an expected accuracy may be predetermined before training the DCNN model. The batch selection and updating of the DCNN model parameters are performed repeatedly until the accuracy of the output 2D and/or 3D label maps meets the expected accuracy.

As described above, training data may be received and preprocessed in step 1105. Training system 1010 may be configured to input the selected batch of training data to a DCNN model for training in step 1110. Training system 1010 may employ the DCNN model with its current parameters, e.g., weights of the filters, to calculate an output map corresponding to the input stacks of origin medical images. In some embodiments, the action of the DCNN model may be symbolically captured by the function $Y^*=f(X; \theta)$, where $Y^*$ is the calculated output of the DCNN model and $\theta=(\theta_1, \theta_2, \ldots, \theta_L)$ are the parameters of the DCNN model. The DCNN is trained using data sets $\{X, Y\}_i$, $i=1, \ldots, N$, where $X_i$ comprises input image data (e.g., medical images, anatomy maps, functions of images or anatomy maps, planning metadata) and $Y_i$ is the corresponding output map.

In Step 1120, training system 1010 may compare the calculated output map with the training data received in step 1105, and calculate corresponding error maps. Training system 1010 may determine or update $\theta$ based on the obtained error maps in step 1120. For example, a back-propagation method may be used to determine or update the $\theta$ based on the difference between the calculated output map and the training map. The back-propagation method may optimize the parameters by minimizing a loss function with respect to parameters in the DCNN model. One skilled in the art would be familiar with various loss functions, such as the mean absolute error (MAE) of the model prediction or $L_1$ norm $J(\theta^*)=\arg\min_\theta \|Y-Y^*\|_1$, or the mean squared error (MSE) or $L_2$ norm $J(\theta^*)=\arg\min_\theta \|Y-Y^*\|_2$ where $\theta^*$ comprises the choice of parameters that minimizes the differences between Y and $Y^*$. A back-propagation algorithm may be used to compute the gradient of the error function with respect to the model parameters or weights. Then $\theta$ may be updated iteratively using a stochastic gradient descent algorithm to converge on $\theta^*$.

In some aspects, the cost functions may express the data approximation function as a probabilistic function of the problem variables, or the conditional likelihood of observing Y given X and subject to the values of the parameters $\theta$, expressed as $P(Y|X; \theta)$, for which the optimal parameters $\theta_{ML}$ are obtained by maximizing the likelihood $\theta_{ML}=\arg\max_\theta P(Y|X; \theta)$, or alternatively $\theta_{ML}=\arg\max_\theta \Sigma_{i=1}^T \log P(Y|X; \theta)$, summed over the training data. However expressed, the optimal $\theta$ is determined by back-propagation In step 1125, training system 1010 may determine whether a stopping criteria is satisfied. As described above, in some embodiments a stopping criterion may be expressed as a maximum number of iterations. So, for example, training system 1010 may determine whether an iteration index is equal to or greater than a predetermined maximum number index. Additionally or alternatively, training system 1010 may determine whether the accuracy of the output maps meet or exceeds the expected accuracy, e.g., by determining whether the loss function is smaller than a threshold. If training system 1010 determines that a stopping criteria has not been satisfied, process 1100 may return to step 1105 and receive training data, or generate a new training data from previously received training data, for training the DCNN model. If training system 1010 determines that the criteria for stopping the iteration has been met, training process 1100 may proceed to step 1130, in which training system 1010 may be configured to save the DCNN model with the updated parameters and/or output the trained DCNN model.

In some embodiments, more than one training image datasets (e.g., more than one 3D original medical image and corresponding 3D destination medical image, and optionally anatomy map and/or planning metadata) may be used for training the DCNN model. In such instances, when receiving training data in step 1105, training system 1010 may be configured to select one or more training image datasets, and then select (or generate) input data. Steps 1110 to 1125 may then proceed similarly as described above.

Exemplary DCNN Model-Based Output Map Generation Processes

Exemplary output map generation processes performed by the disclosed systems and methods are described in detail below with references to FIG. 12, which depicts a flowchart illustrating an exemplary output map generation process 1200. Output map generation process 1200 may be performed by prediction system 1020.

As shown in FIG. 12, prediction system 1020 may be configured to receive a trained DCNN model (e.g., neural network 920) in step 1210. The trained DCNN model may be obtained through process 1100 described with regard to FIG. 11, or through another process. Prediction system 1020 may be configured to perform output map generation process 1200 for a specific viewpoint, such as along a specific anatomical plane. For example, prediction system 1020 may be configured to select among the three anatomical planes, such as the axial plane, sagittal plane, and coronal plane. The received trained DCNN model may have been trained with slices (or stacks of slices) along the selected anatomical plane, or may have been trained with slices (or stacks of slices) along multiple anatomical planes including the selected anatomical plane.

In step 1220, prediction system 1020 may be configured to receive input data. The input data may comprise one or more medical images. The one or more medical images may comprise one or more 3D medical images. The 3D medical images may depict at least a portion of the head, torso, abdomen, limbs, or other anatomical areas of a patient. Prediction system 1020 may be configured to preprocess the origin medical images. For example, when the medical images comprise one or more 3D medical images, prediction system 1020 may be configured to convert the one or more 3D medical images to one or more stacks of 2D medical images. As described above, the one or more stacks of 2D medical images may be sequential and may have one or more overlapping images, such that the middle images of the stacks together substantially constitute the whole 3D medical image.

Prediction system 1020 may be configured to select a plane of the 3D image received in step 1220, and may be configured to generate one or more stacks of origin medical images based on the received input data and the selected plane. In some aspects, prediction system 1020 may generate slices from one or more of the medical images along the selected anatomical plane. In various aspects, prediction system 1020 may generate slices from one or more of the anatomy images along the selected anatomical plane. In some aspects, prediction system 1020 may generate a sequence of individual medical slices, or optionally anatomy slices. In various aspects, prediction system 1020 may generate a sequence of stacks of slices, with a middle slice in each stack corresponding to the generated output map.

In some embodiments, prediction system 1020 may be configured to generate output maps using the same type of medical images the DCNN model is trained on. For example, prediction system 1020 may be configured to generate output maps from images acquired using the same imaging modality as the training images. For example, when the DCNN model is trained on CT images, the prediction system 1020 may be configured to generate output map using CT images. When the DCNN model is trained on 3D CT images, the prediction system 1020 may be configured to generate output map using 3D CT images. Furthermore, when the DCNN model is trained on stacks of adjacent medical images, prediction system 1020 may be configured to apply the model to the same type of stacks of adjacent medical images.

In some embodiments, prediction system 1020 may be configured to generate output maps for a current patient having the same general diagnosis as the patients from whom the training data was gathered. For example, the current patient may have the same type of cancer, and/or a tumor in the same location as the patients from whom the training data was gathered.

In some embodiments, prediction system 1020 may be configured to generate output maps using the same type of anatomy maps the DCNN model is trained on. For example, when the DCNN model is trained on anatomy maps that associate pixels or voxels with critical structures and targets, the prediction system 1020 may be configured to generate output maps using anatomy maps that similarly associate pixels or voxels with critical structures and targets.

In step 1230, the trained DCNN model is applied to the input data. The prediction system 1020 may determine an output map using the input data, as described above with regards to FIGS. 8 to 11. In step 1240, output map generation process 1200 may further comprise prediction system 1020 outputting one or more output maps. For example, prediction system 1020 may be configured to output the output map generated in step 1230. Outputting may comprise displaying the one or more output maps for further analysis or observation, storing the one or more output maps in a non-transitory medium, or providing the one or more output maps to a computer process, program, and/or application. The non-transitory medium and computer process, program, and/or application may be on a remote system.

In some embodiments, prediction system 1020 may be configured to assemble the one or more output maps into a 3D output maps. As described above, prediction system 1020 may be configured to process input data along two or more of the three anatomical planes. In such instances, process 1200 may include generating a final 3D output map. In some aspects, prediction system 1020 may be configured to determine the final 3D output map by fusing the two or more 3D output map determined for the two or more anatomical planes. In some embodiments, the value of a voxel of the fused 3D output map may be an average value. As a non-limiting example, when the three fused 3D output maps have fluence values of 0.7, 0.8, and 0.3, the voxel may then have a CT value of 0.6. As described herein, any suitable methods may be used to fuse the three 3D output maps determined in output map generation process 1200.

Data Preparation, Neural Network Training, and Evaluation of Trained Neural Network for Prostate Radiotherapy A database of medical images for 178 prostate patients was selected as training data. Prostate radiation therapy treatment plans were prepared for each patient to serve as the expected results in the training data, as follows. First, contours (outlines of the relevant anatomy objects) were reviewed and many were redrawn to conform to the combined anatomy guidelines of the Radiation Therapy Oncology Group and RTOG Foundation Inc. (www.rtog.org/). Clinical treatment volumes (CTVs) and planning treatment volumes (PTVs) were then generated for each patient using a margining tool in Monaco®. The radiation therapy plans were then for each patient using the Erasmus iCycle treatment planning program. This program applies multi-criterial plan optimization over a rank-ordered list of hard constraints and prioritized objectives specifying the target coverage and organ-at-risk (OAR) sparing goals of the physician. The completed plans with dose maps were computed by Elekta Monaco using the iCycle plan as a template, and image, structure, plan, and dose files were stored in DICOM format. The medical images were divided into a training set of 165 patients and a testing set of 13 patients. The 13 test cases were selected at roughly equal intervals across the entire set, aiming to sample the variance inherent in data that were longitudinally acquired over several years.

The medical images for the patients in the Training Data varied in many respects. They displayed a range of disease features, from very small to very large prostate-seminal vesicle treatment volumes. They varied in pixel density and slice thickness (from 1.25 to 3 mm). The location of the target area within the field-of-view also varied. To minimize these sources of variability, data were resampled to the same 3D grid size and spacing, and targets were re-located to be consistently placed within the field-of-view. Data were first translated from DICOM to ITK formats. In one particular configuration, the image, structures, and dose data were then resampled to an (x, y, z)=(256, 256, N) grid with voxel spacing of 2.25×2.25×2.25 mm, where N is the number of axial slices required to span the 3D dose distribution along the z axis. The PTV center of mass is located first, and then the dose is transformed consistent with the PTV at the axial center. The z-span of the dose is measured, and N resampled CT images are produced at the same z-locations as the dose slices. The data were then translated back to DICOM format.

Bowel gas appeared as voids in medical images presented to a neural network. This produced artifacts in the estimated dose distributions. In further preparation for DCNN training, gas voxels were identified and their intensities were replaced by values randomly-sampled from a soft tissue intensity range, and the processed images were presented to the neural network. The previously observed artifacts were no longer present in the estimated dose distributions.

Anatomy images of several formats were considered and presented to a neural network model, including signed distance maps that detail the nearest distance to an anatomy object's boundary, the CT images themselves, enhanced versions of the images (Laplacian sharpened, inverted), and Sobel edge-detected versions of the CT images. Further, 3D reconstruction was applied to these images to determine a patient external contour, and signed distance maps for each view.

Figure 14:
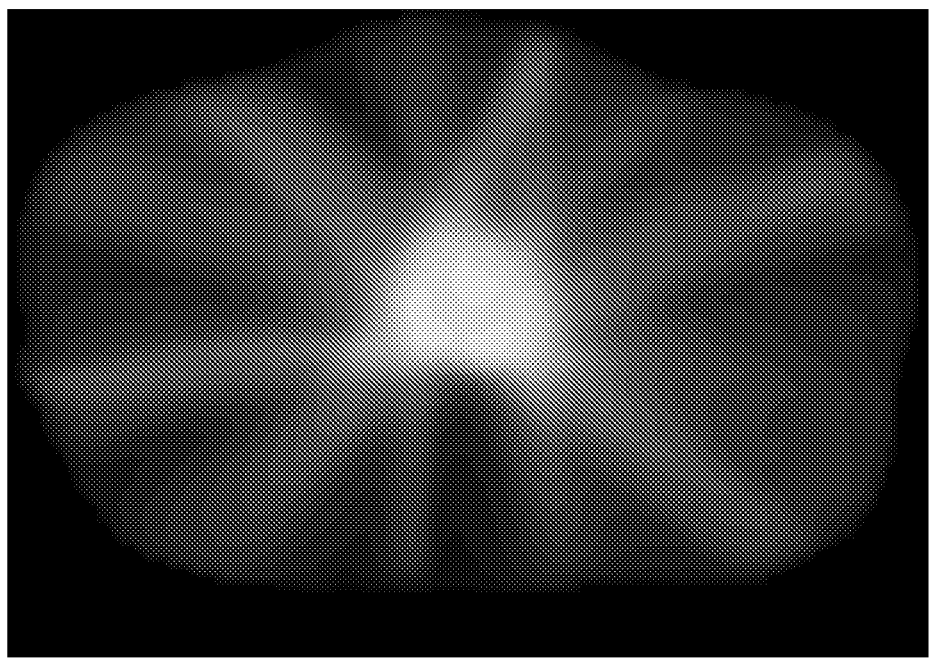
FIG. 14 illustrates an axial view of an exemplary radiation dose distribution to the human prostate of FIG. 13, according to an embodiment of the present disclosure.

While the RGB channel layers of a DCNN often are used to specify color data of an image that is being input to a DCNN, embodiments of the present invention utilize the RGB channel layers in a novel way. Using three separate but related images, RGB channels of the DCNN may be populated with an image relating to the patient's external contour signed distance map, the corresponding axial signed distance map of the organs at risk, and the signed distance map of the patient's planning treatment volume. Once the three RGB channels are so populated, a composite color image can be used for training the DCNN. The expected results to be used in the training are shown in FIG. 14, as described below, which corresponds to pre-established "gold standard" treatment plan for this patient. The DCNN will now be trained (see description of FIGS. 7 and 11 above describing training process) with the training image 13 and the expected results as shown in FIG. 14, with the goal to select a proper number of training iterations and learning rate parameters to allow the learning algorithm to converge upon a network configuration that produces a fluence map that is suitably similar to the expected result and satisfies other diagnostic criteria.

Figure 13:
FIG. 13 illustrates a CT section of a prostate.

FIG. 13 depicts the axial CT view with was further analyzed in the figures that follow. FIG. 14 shows the selected axial view corresponding to the expected (ground truth) dose that is to be used for testing trained network accuracy using a patient's anatomy and treatment information. The expected results to be used in the training, which corresponds to pre-established "gold standard" treatment plan for this patient.

Initial Training—Grid Voxel Spacing of 2.25 mm×2.25 mm×2.25 mm

The network model selected was the U-Net described by Ronneberger, O., Fischer, P. and Brox, T., U-Net: Convolutional networks for biomedical image segmentation, arXiv: 1505.0459/v1, 2015, which is incorporated by reference herein in its entirety. This network merges learned features at several scales with unpooled features at the same scale.

This network was model was used on the open-source Caffe platform, described in Jia, Y., Shelhammer, E., Donahue, J., Karayev, S., Girshick, R., Guadarrama, S., Darrell, T., Caffe: Convolutional architecture for fast feature embedding, arXiv:1408:5093v1, 2014, which is incorporated by reference herein in its entirety. The input image and dose sizes were 256×256 and the "augmentation" option was selected. With this option, Caffe randomly crops a 224×224 central portion of the image and dose pair, presenting the data to the network with a random offset in order to reducing overfitting.

A program was written that accepts the 2D dose image output from Caffe and reconstructs the DICOM dose object in a native DICOM dose file. That dose was added to an existing DICOM patient's dataset, and read into the Monaco program for comparison with the Erasmus-iCycle program's dose. Dose volume histograms (DVHs) plotting % of anatomy object's volume (ordinate) versus % of anatomy object covered by dose (abscissa) were used to evaluate the results.

The training set was presented to the DCNN model on computers equipped with an nVidia graphics processor unit. The learning rate was initially set at 0.01, and this rate was reduced by factor of 0.1 every 30,000 iterations. A computer with the nVidia TitanX card completed about 10,000 iterations/day, and a computer with the nVidia Tesla card completed 3,000 iterations/day. Each of the images in the testing set was then presented to each of the trained models. The network provided robust and viewable dose estimates. This was true for both the larger and the smaller iteration counts (e.g., about 10 k iterations) in training.

Figure 15:
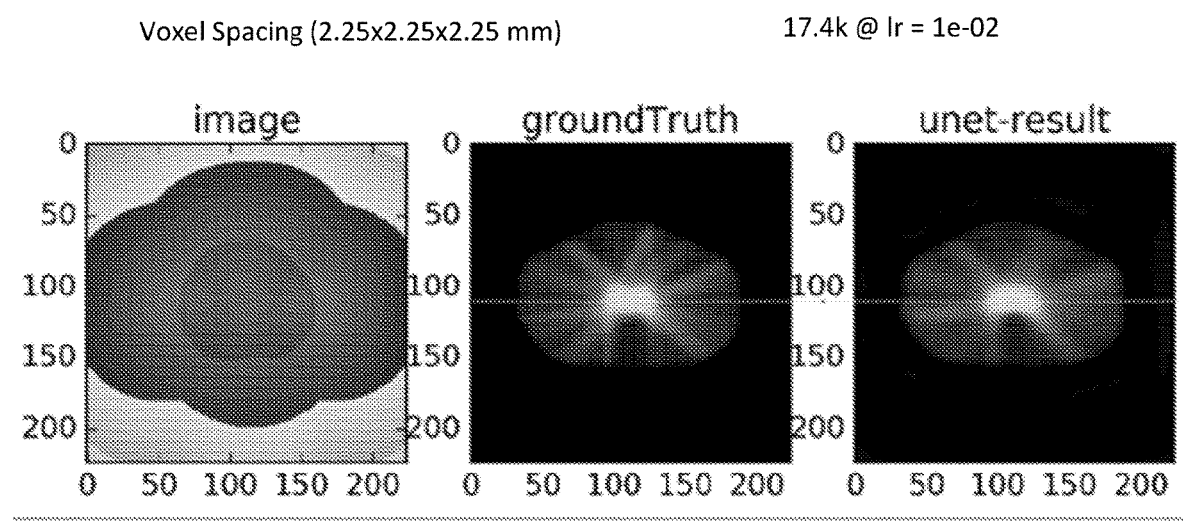
FIG. 15 illustrates (left to right, respectively) a patient a signed distance map, an expected dose distribution and an estimated dose distribution at 17,000 training iterations.

To perform training, initially a learning rate was set at 0.01, and 17,400 training iterations were used to train the deep learning model to produce the results shown in FIG. 15, with the left side of the illustration showing the input image, the middle image showing the ground truth or expected results that were input to the training algorithm, and the rightmost image labeled as "unet-result" shows the predicted result output map (fluence map) corresponding to the input data that the DCNN produced after completing 17,400 training iterations.

Figure 16:
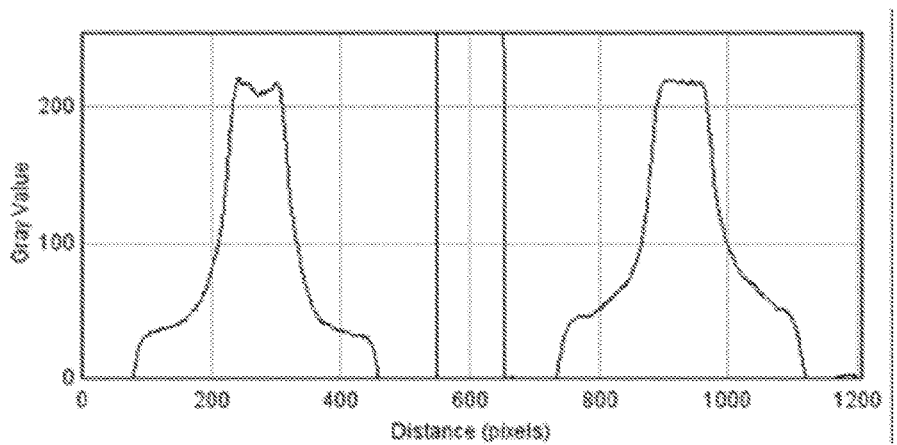
FIG. 16 illustrates intensity profiles for the expected and estimated dose distributions of FIG. 15.

FIG. 16 depicts dose profiles of the expected results (left image) and the predicted results (right image). Visual inspection of FIG. 16 shows a reasonable approximation of the predicted results to the expected results with this training set (2.25 mm×2.25 mm×2.25 mm voxel spacing, 17,400 interactions, and learning rate of 0.01).

Figure 17:
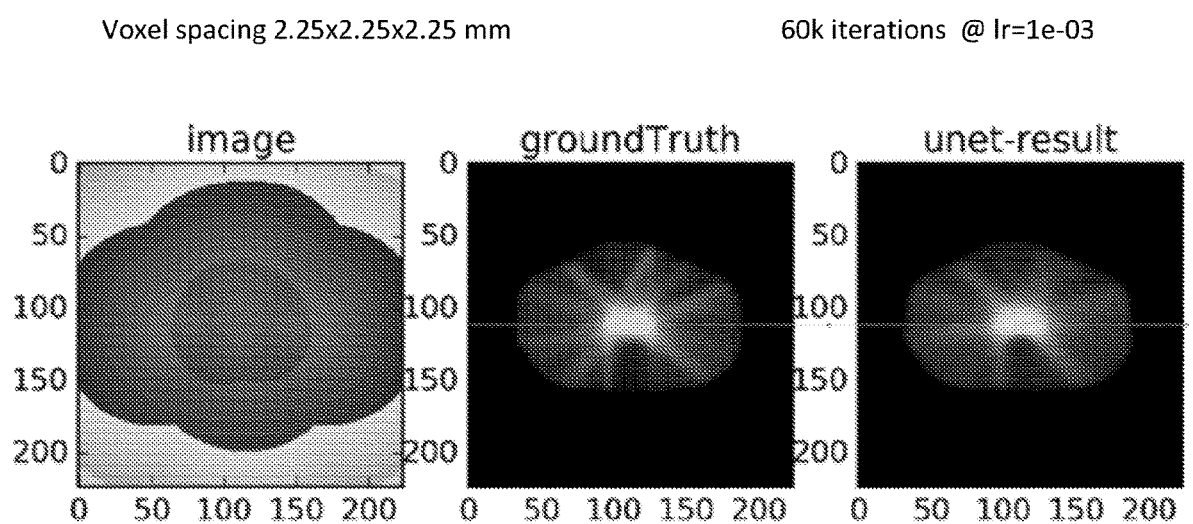
FIG. 17 illustrates (left to right, respectively) a patient a signed distance map, an expected dose distribution and an estimated dose distribution at 60,000 training iterations.
Figure 18:
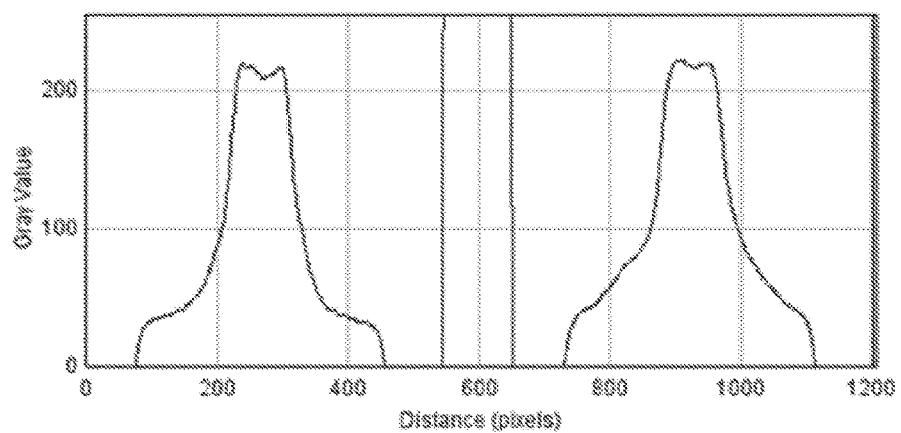
FIG. 18 illustrates intensity profiles for the expected and estimated dose distributions of FIG. 17.

FIG. 17 illustrates the state of the training scenario for the same training data now at 60,000 iterations and with learning rate now at 0.001. The predicted output (fluence map) shown on the right of FIG. 17 more closely approximates the ground truth expected result in the middle of FIG. 17 than the previous FIG. 15, where only 17,400 iterations were used. Correspondingly, the dose histograms in FIG. 18 show a closer match between the expected results (left) and the predicted output (right), especially in the dipped peak of the curves when compared to FIG. 16.

Figure 19:
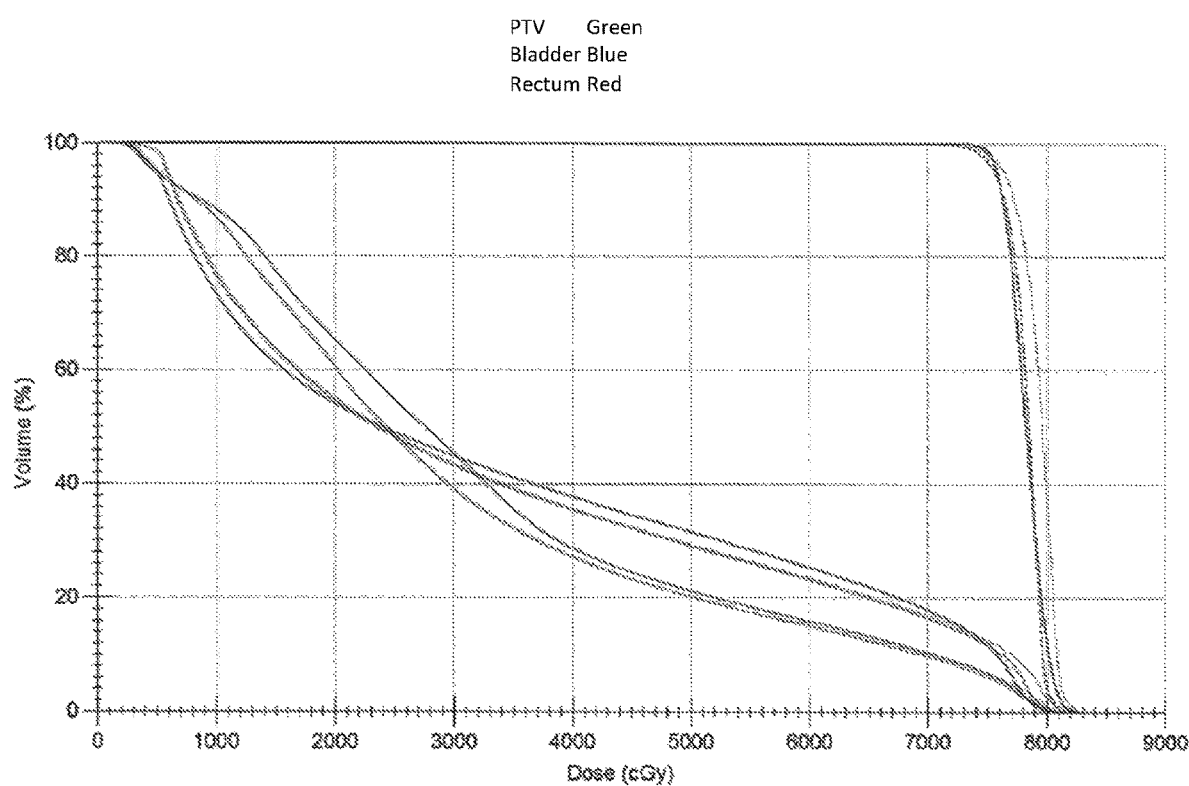
FIG. 19 illustrates a dose volume histogram (DVH) for various numbers of iterations, where voxel spacing and learning rate remained the same, according to some embodiments of the present disclosure.

A Dose Volume Histogram (DVH) was prepared (shown in FIG. 19) for various numbers of iterations, where voxel spacing and learning rate remained the same. 10 k, 20 k, 60 k, and 90 k iterations were used in different training trials, and the histogram show a very close fit between the ground truth data and the expected results at a 90 k iteration training cycle. In the DVH, PTV is represented in green, bladder plots are blue, and rectum plots are red. If the predicted results of the training algorithm matches the ground truth (or expected results) exactly, the DVH curves for the ground truth and the particular number of iterations producing the optimized predicted results would be essentially identical. The number of training iterations to use, along with the voxel spacing size and learning rates may be determined experimentally by examining how closely the DVH plots for intervals of training time converge to the predicted result.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer-readable storage medium may cause a machine to perform the functions or operations described, and includes any mechanism that stores information in a form accessible by a machine (e.g., computing device, electronic system, and the like), such as recordable/non-recordable medium (e.g., read only memory (ROM), random access memory (RAM), magnetic disk storage medium, optical storage medium, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general-purpose computer selectively activated or reconfigured by a computer program stored in the computer. Such a computer program may be stored in a computer-readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of medium suitable for storing electronic instructions, each coupled to a computer system bus.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be interpreted as open ended, such that an item or items following any one of these words is not meant to be an exhaustive listing of the item or items, or meant to be limited to only the listed item or items. And the singular forms "a," "an," and "the" are intended to include plural references, unless the context clearly dictates otherwise.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A radiation therapy treatment system to predict a radiation therapy dose, comprising:
    an image acquisition device to acquire one or more three-dimensional medical images;

a non-transitory machine-readable medium to store the one or more three-dimensional medical images, a neural network model, one or more three-dimensional anatomy maps and one or more three-dimensional dose distributions; and an image processing device configured to:

train the neural network model to predict both a fluence map and a dose map based on the one or more three-dimensional medical images and the one or more three-dimensional anatomy maps, the fluence map depicting a number of particles per second of applied radiation crossing a volume element in a patient, and the dose map depicting a radiation dose to be delivered to a patient from a radiotherapy device at a particular location; and generate a new three-dimensional dose distribution based on both the fluence map and the dose map predicted by the neural network model.

2. The system of claim 1, wherein the one or more three-dimensional anatomy maps correspond to a subset of the one or more three-dimensional medical images and indicate locations of anatomical structures and locations of one or more treatment targets.

3. The system of claim 1, wherein the one or more three-dimensional anatomy maps comprise at least one of an image contour, a contoured surface in space, a map of functional anatomy, a binary mask corresponding to a structure, and a function of the structure comprising a signed distance map.

4. The system of claim 1, wherein the trained neural network model provides a three-dimensional map of fluence comprising the fluence map.

5. The system of claim 1, wherein the image processing device is further configured to:

(a) initialize the neural network model with an initial layer configuration, an initial connection configuration, an initial set of weights, and an initial set of biases;

(b) input a first set of training data of a plurality of training data to the initialized neural network model, the first set of training data comprising patient records from a population of patients that include medical images, specific anatomical structures, and expected three-dimensional dose distributions;

(c) receive a predicted dose distribution from the neural network model;

(d) compare the predicted dose distribution from the neural network model with one of the expected dose distributions and adjust weights and biases of the neural network model to decrease differences between the predicted dose distribution and the one of the expected dose distributions;

iterate steps (c) through (d) until the differences between the predicted dose distribution and the one of the expected dose distributions reach a predetermined threshold; and store the trained neural network model in the non-transitory machine-readable medium.

6. The system of claim 5, wherein the plurality of training data comprises a second set of training data, and the second set of training data comprises an updated set of new patient images corresponding to a particular patient.

7. The system of claim 5, wherein the plurality of training data comprises at least one of a dose distribution a measure of quality based on a dose volume histogram, an image contour, a contoured surface in space, functional anatomy, and a signed distance map and combinations thereof to train the initialized neural network model.

8. The system of claim 5, wherein the plurality of training data comprises a function of the predicted dose distribution, wherein the function is at least a square or an exponential.

9. The system of claim 5, wherein the image processing device is configured to:

receive the trained neural network model stored in the non-transitory machine-readable medium;

input testing data into the trained neural network model, the testing data comprising new patient records from a new population of patients that include new medical images, new specific anatomical structures, and new expected dose distributions;

obtain an additional new predicted dose distribution from the trained neural network model; and determine an error factor by comparing the new expected dose distributions with the additional new predicted dose distribution.

10. The system of claim 1, wherein the neural network model comprises a deep convolutional neural network (DCNN).

11. A method to predict a radiation therapy dose, the method comprising:

receiving one or more three-dimensional medical images from an image acquisition device;

storing the one or more three-dimensional images, a neural network model, one or more three-dimensional anatomy maps, and one or more three-dimensional dose distributions in a non-transitory computer-readable medium;

training, by at least one processor, the neural network model to predict both a fluence map and a dose map based on the one or more three-dimensional medical images and the one or more three-dimensional anatomy maps and the one or more three-dimensional dose distributions, the fluence map depicting a number of particles per second of applied radiation crossing a volume element in a patient, and the dose map depicting a radiation dose to be delivered to a patient from a radiotherapy device at a particular location; and generating a new three-dimensional dose distribution based on both the fluence map and the dose map predicted by the neural network model.

12. The method of claim 11, wherein the one or more three-dimensional anatomy maps correspond to a subset of the one or more three-dimensional medical images and indicate locations of anatomical structures and treatment targets.

13. The method of claim 11, wherein the one or more three-dimensional anatomy maps comprise at least one of an image contour, a contoured surface in space, a map of functional anatomy, a binary mask corresponding to a structure, and a function of the structure comprising a signed distance map.

14. The method of claim 11, wherein the fluence map comprises a three-dimensional map of fluence.

15. The method of claim 11, wherein training the neural network model comprises:

(a) initializing the neural network model with an initial layer configuration, an initial connection configuration, an initial set of weights, and an initial set of biases;

(b) inputting a first set of training data of a plurality of training data to the initialized neural network model, the first set of training data comprising patient records from a population of patients that include medical images, specific anatomical structures, and expected three-dimensional dose distributions;

(c) receiving a predicted dose distribution from the neural network model;

(d) comparing the predicted dose distribution from the neural network model with one of the expected dose distributions and adjust weights and biases of the neural network model to decrease differences between the predicted dose distribution and the one of the expected dose distributions;

iterating steps (c) through (d) until the differences between the predicted dose distribution and the one of the expected dose distributions reach a predetermined threshold; and storing the trained neural network model.

16. The method of claim 15, wherein the plurality of training data comprises a second set of training data, and the second set of training data comprises an updated set of new patient images corresponding to a particular patient.

17. The method of claim 15, wherein the plurality of training data comprises at least one of a dose distribution, a measure of quality based on a dose volume histogram, an image contour, a contoured surface in space, functional anatomy, and a signed distance map and combinations thereof to train the initialized neural network model.

18. The method of claim 15, wherein the plurality of training data comprises a function of the predicted dose distribution, wherein the function is at least a square or an exponential.

19. The method of claim 15, further comprising:

receiving the trained neural network model;

inputting testing data into the trained neural network model, the testing data comprising new patient records from a new population of patients that include new medical images, new specific anatomical structures, and new expected dose distributions;

obtaining an additional new predicted dose distribution from the trained neural network model; and determining an error factor by comparing the new expected dose distributions with the additional new predicted dose distribution.

20. The method of claim 15, wherein the neural network model comprises a deep convolutional neural network (DCNN).

21. A non-transitory computer-readable medium comprising computer-readable instructions that, when executed by one or more processors, configure the one or more processors to perform operations comprising:

receiving one or more three-dimensional medical images from an image acquisition device;

storing the one or more three-dimensional images, a neural network model, one or more three-dimensional anatomy maps, and one or more three-dimensional dose distributions in a non-transitory computer-readable medium;

training the neural network model to predict both a fluence map and a dose map based on the one or more three-dimensional medical images and the one or more three-dimensional anatomy maps and the one or more three-dimensional dose distributions, the fluence map depicting a number of particles per second of applied radiation crossing a volume element in a patient, and the dose map depicting a radiation dose to be delivered to a patient from a radiotherapy device at a particular location; and generating a new three-dimensional dose distribution based on both the fluence map and the dose map predicted by the neural network model.

22. The non-transitory computer-readable medium of claim 21, wherein the one or more three-dimensional anatomy maps correspond to a subset of the one or more three-dimensional medical images and indicate locations of anatomical structures of the patient and locations of one or more treatment targets.

* * * * *

UNITED STATES PATENT AND TRADEMARK OFFICE
CERTIFICATE OF CORRECTION

PATENT NO. : 11,850,445 B2
APPLICATION NO. : 16/330662
DATED : December 26, 2023
INVENTOR(S) : Lyndon Stanley Hibbard Page 1 of 1

It is certified that error appears in the above-identified patent and that said Letters Patent is hereby corrected as shown below:

In the Claims

In Column 35, Line 63, in Claim 7, delete "distribution" and insert --distribution,-- therefor Signed and Sealed this
Eighteenth Day of February, 2025

Coke Morgan Stewart
*Acting Director of the United States Patent and Trademark Office*